United States Patent [19]

Bushnell et al.

[11] Patent Number: 5,768,853
[45] Date of Patent: Jun. 23, 1998

[54] DEACTIVATION OF MICROORGANISMS

[75] Inventors: Andrew H. Bushnell, San Diego, Calif.; Håkan Möller, Lund, Sweden; R. Wayne Clark, Del Mar, Calif.; Miriam Gersten, San Diego, Calif.; Don Meader, San Diego, Calif.; Lars-Åke Näslund, Furulund, Sweden; Håkan Mellbin, Hörby, Sweden; Pär Olanders, Genarp, Sweden; Olof Stark, Ystad, Sweden

[73] Assignee: Purepulse Technologies, Inc., San Diego, Calif.

[21] Appl. No.: 614,854

[22] Filed: Mar. 12, 1996

Related U.S. Application Data

[63] Continuation-in-part of Ser. No. 599,558, Feb. 15, 1996, abandoned.

[51] Int. Cl.⁶ .................................................. B65B 55/00
[52] U.S. Cl. .............................................. 53/167; 53/141
[58] Field of Search .......................... 53/127, 141, 167, 53/425, 426; 422/22, 23, 24; 426/238, 248

[56] References Cited

U.S. PATENT DOCUMENTS

| | | |
|---|---|---|
| 2,072,416 | 3/1937 | Berndt et al. . |
| 2,072,417 | 3/1937 | Berndt et al. . |
| 2,482,507 | 9/1949 | Rentschler et al. . |
| 2,930,706 | 3/1960 | Moulton . |
| 3,814,680 | 6/1974 | Wood . |
| 3,817,703 | 6/1974 | Atwood . |
| 3,934,044 | 1/1976 | Busch, et al. . |
| 3,955,921 | 5/1976 | Tensmeyer . |
| 4,035,981 | 7/1977 | Braun et al. . |

(List continued on next page.)

FOREIGN PATENT DOCUMENTS

| | | |
|---|---|---|
| 7502834 | 3/1975 | Netherlands . |
| 1052513 | 12/1963 | United Kingdom . |
| 1346521 | 2/1974 | United Kingdom . |
| 1448411 | 9/1976 | United Kingdom . |
| 1548997 | 7/1979 | United Kingdom . |
| 1581998 | 12/1980 | United Kingdom . |

OTHER PUBLICATIONS

Johnson, "Flashblast—the light that cleans", *Popular Science*, pp. 82–84.

Rentschler, et al., "Bactericidal Effect of Ultraviolet Radiation", *Research Department, Westinghouse Lamp Divison*, Bloomfield, New Jersey, pp. 745–774, Oct., 1940.

*Primary Examiner*—Daniel Moon
*Attorney, Agent, or Firm*—Fitch, Even, Tabin & Flannery

[57] ABSTRACT

Methods and apparatuses are described for food product preservation by deactivation of microorganisms and enzymes by applying high-intensity, short-duration pulses of polychromatic light in a broad spectrum to packaging material surfaces. In some embodiments, a photodiode is employed for detecting the intensity of the light, and a control circuit is used to adjust power delivered to a flashlamp if the intensity of the light needs adjustment. In some embodiments, an outer safety glass is employed to protect the flashlamps. The outer safety glass may include coating materials at ends thereof. In addition, several variations of lamp assembly geometries accommodate small diameter packaging material tubes by, for example, using an fill pipe having offset first and second portions with a transitional region thereinbetween, or be eliminating the water jackets and using an outer safety glass to contain water as it is passed over flashlamps. In another additional embodiment, a lamp holding device includes a holding cylinder with a first flange, which, together with a compression cylinder, compresses the first O-ring into the flashlamp. In yet another embodiment, a lamp holding device is positioned in a receptacle into which an electrode of a U-lamp is inserted. The lamp holding device allows a proximal portion to move relative to a distal portion thereof. In yet a further embodiment, a light guide is positioned to receive light emitted from a linear flashlamp and to transmit such light into a packaging material cup.

27 Claims, 19 Drawing Sheets

U.S. PATENT DOCUMENTS

| | | |
|---|---|---|
| 4,042,325 | 8/1977 | Tensmeyer . |
| 4,265,747 | 5/1981 | Copa et al. . |
| 4,391,080 | 7/1983 | Brody et al. . |
| 4,396,582 | 8/1983 | Kodera . |
| 4,424,188 | 1/1984 | DiGeronimo . |
| 4,464,336 | 8/1984 | Hiramoto . |
| 4,494,357 | 1/1985 | DiGeronimo . |
| 4,871,559 | 10/1989 | Dunn et al. . |
| 4,910,942 | 3/1990 | Dunn et al. . |
| 5,034,235 | 7/1991 | Dunn et al. . |

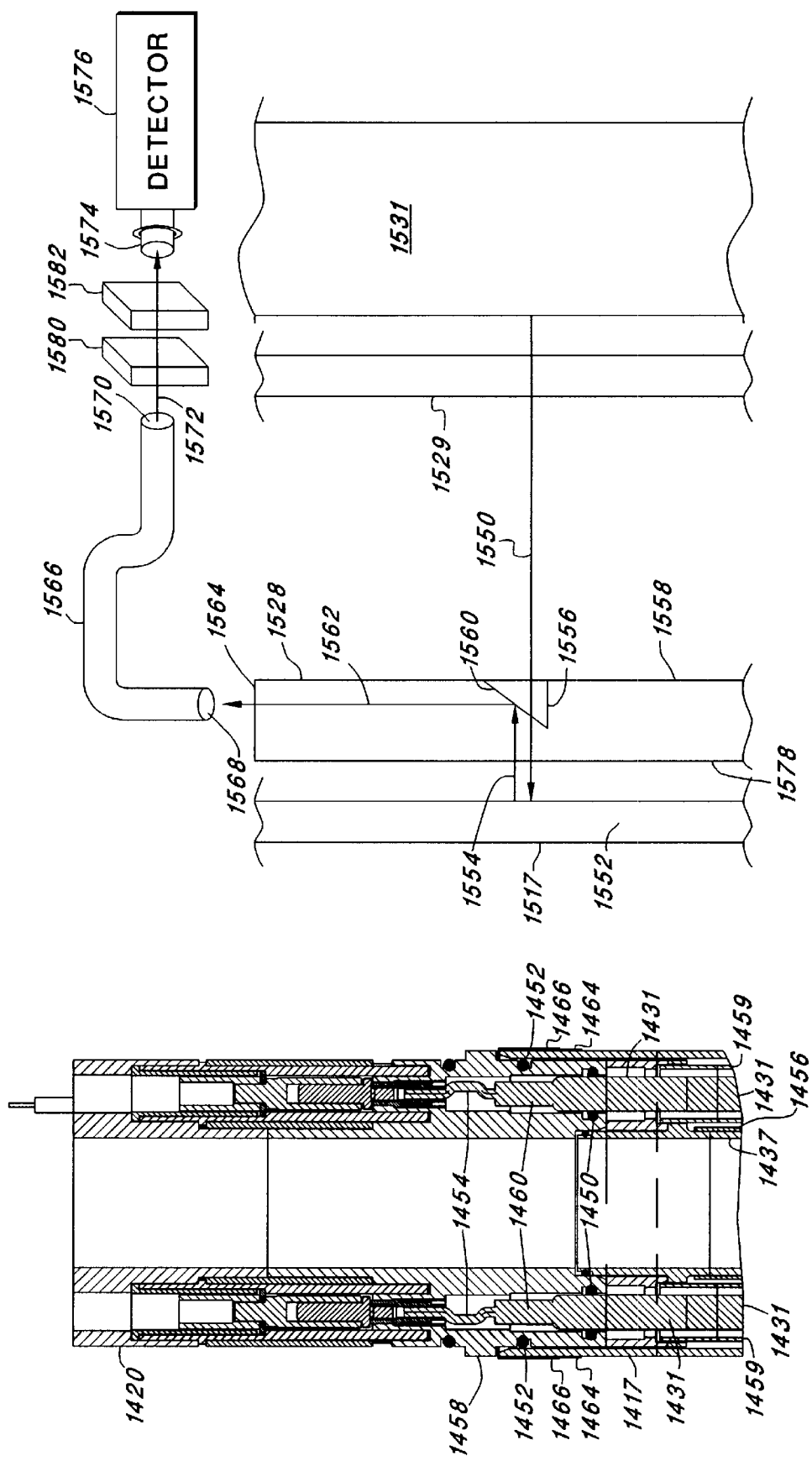

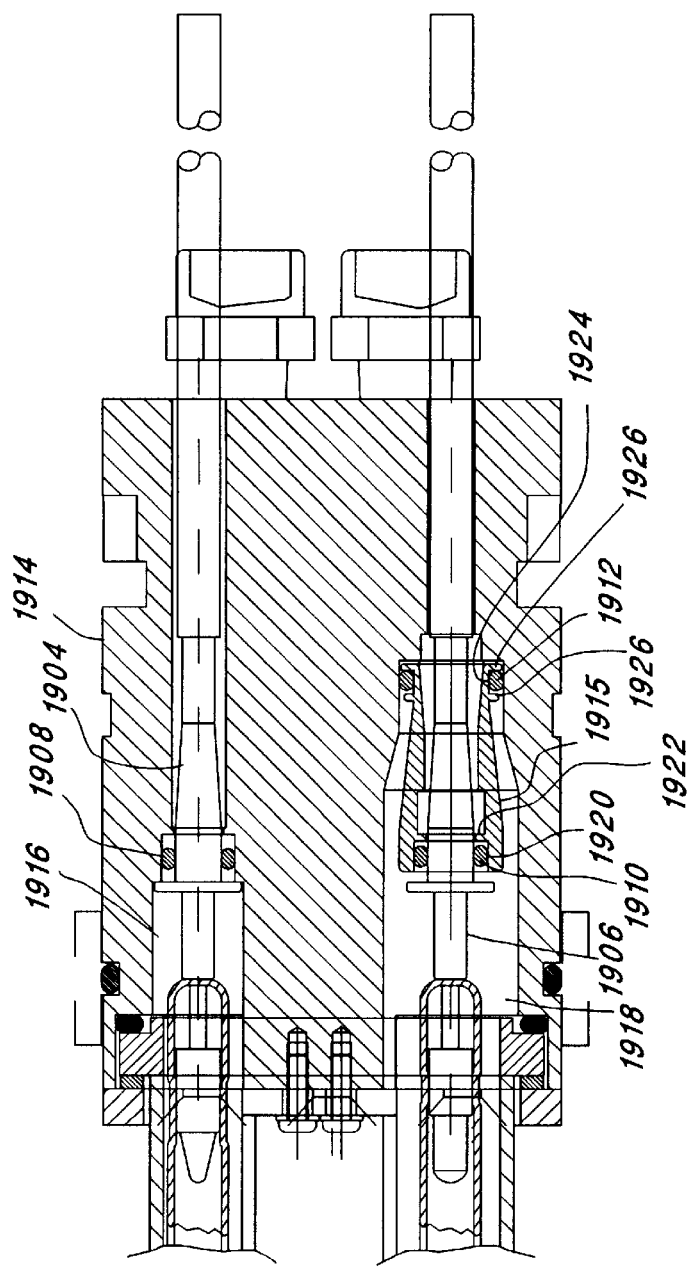
FIG. 19
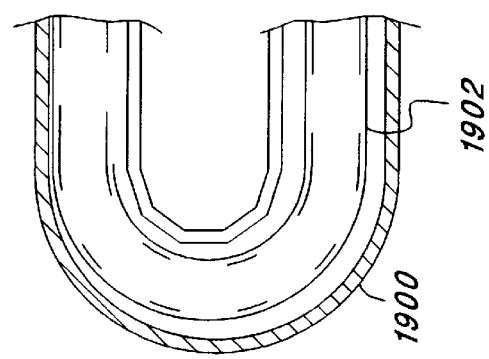

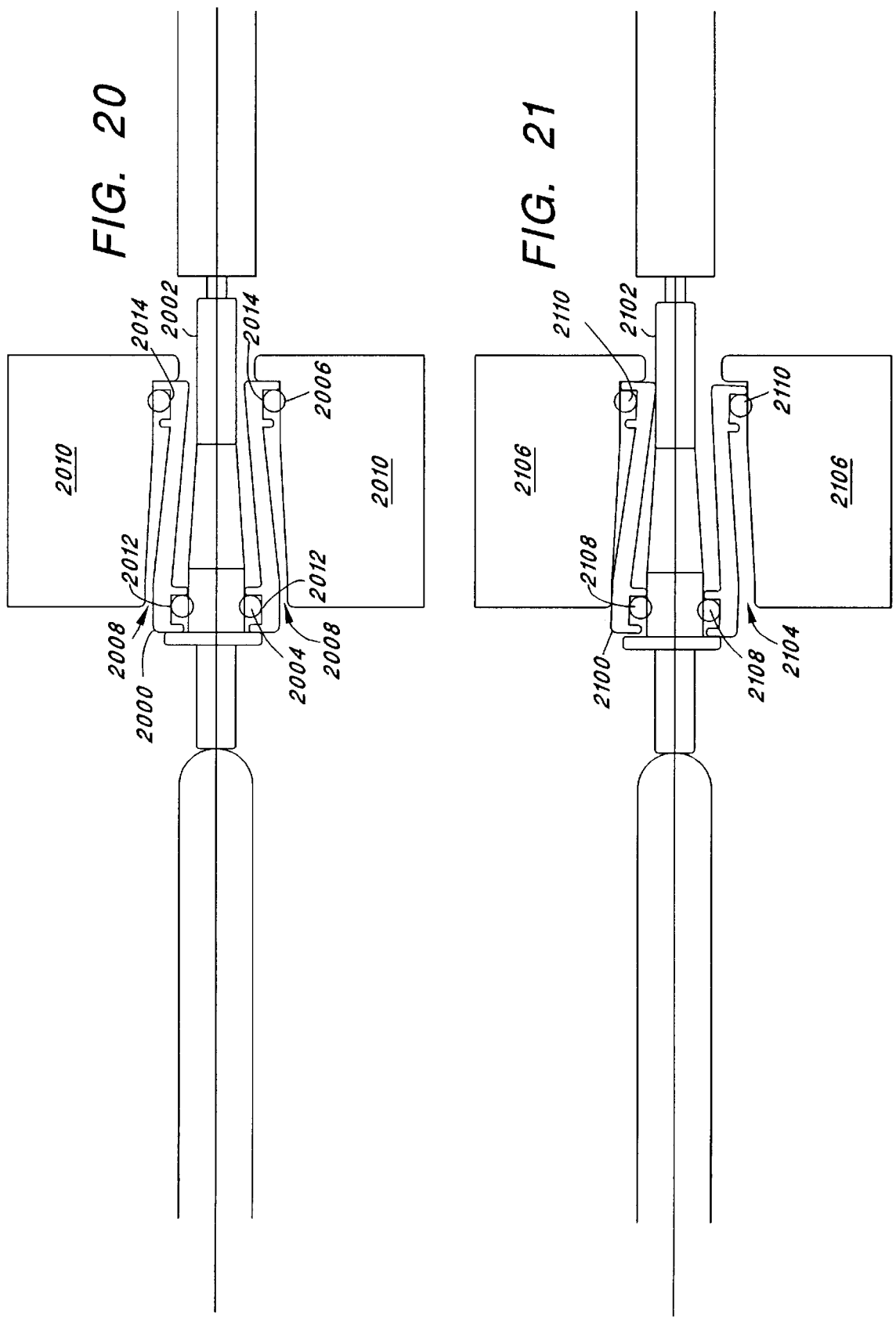

DEACTIVATION OF MICROORGANISMS

This application is a Continuation-in-Part of our earlier application Ser. No. 08/599,558 filed Feb. 15, 1996 now abandoned.

BACKGROUND OF THE INVENTION

The present invention relates to the deactivation of microorganisms, and more particularly to the deactivation of microorganisms using short-duration, high-intensity pulses of broad-spectrum polychromatic light. Even more particularly, the present invention relates to the deactivation of microorganisms in food products, packaging, materials, medical instruments and the like using such pulses of light.

Substantial technical effort has been directed to extending the storage time for foodstuffs and other microbiologically labile products and to preserve these products against microbiological spoilage. Such efforts have involved both the treatment of products and the development of packaging techniques for preservation.

A particular need which exists for methods and apparatuses for sterilizing or reducing the microbiological burden on the surfaces of or within food products, packaging materials, medical instruments, and other products. Such methods and apparatuses may be utilized to reduce or eliminate the need for chemical preservatives. For example, baked goods such as bread may accumulate microorganisms, such as mold spores, from the air after they are baked but before they cool sufficiently to be packaged. Any substantial reheating of the baked goods would excessively dry such goods.

Thus, new methods for surface sterilization of such food products, not involving the reheating of such food products, are desirable.

Food products may also be subject to enzymatic degradation, which limits shelf life of the food product. Enzymatic degradation is particularly rapid and evident for example in the browning of freshly cut potatoes and apples, but has adverse effects in a great variety of foods. Enzymatic degradation may act alone, or in combination with microbially caused deterioration.

One example of a food product for which methods and apparatuses for deactivating microorganisms is needed is fresh fish. Fresh fish has a relatively limited storage time before being subject to microbial and/or enzymatic spoilage, which limits the distribution and marketing of fresh fish products. Methods and apparatuses suitable for extending the shelf life of perishable foods such as fresh fish, and/or poultry, beef and pork are highly desirable.

Also, many products, for example some juices, are now processed through the use of heat under conditions that, in order to produce the desired reduction in biological activity, cause a degradation of the taste and palatability of the treated food product. Methods and apparatuses for reducing or eliminating biological activity without such degradative heating are desirable for providing taste and palatability benefits that increase consumer interest and, thus, market for food products so treated.

Significant research and development effort has recently been directed to aseptic packaging technology for packaging of sterilized food products (including high and low acid foods) in sterile packaging materials, in order to provide preserved food products having an extended shelf life. However, such methods and apparatuses may have various disadvantages such as requiring the extensive use of chemical disinfectants which may leave residual chemical products on the packaging material or foodstuff. New methods and apparatuses for sterilizing food product packaging material and for aseptic packaging are desirable.

One example of an aseptic packaging system in combination with a photobiological food treatment apparatus is shown in U.S. Pat. No. 4,871,559, issued to Dunn et al., for METHODS FOR PRESERVATION OF FOODSTUFFS, issued Oct. 3, 1989, and incorporated herein by reference. Short pulses of incoherent, broad spectrum light. are used to preserve food products against microbial degradative processes. As a result, the teachings of the '559 patent provide significant shelf-life and stability enhancements to the food product. Application or pulses of high-intensity, incoherent polychromatic light provides efficient, effective, high throughput processing and results in many practical and economic advantages. Moreover, the short duration and the spectral range of each pulse permits spatial localization of various of the preservative effects of the light pulses to a thin surface layer such as the surface of the food product or packaging material.

Fresh fruits, vegetables, and other food products, for example, strawberries, accumulate microorganisms, which as used herein includes bacteria, viruses, and fungi, from the air, ground, water and other sources with which they come into contact. These microorganisms, through various known mechanisms, cause the perishable food products to spoil, thereby significantly limiting the shelf-life of the food products. (Shelf-life is the period of time during which the perishable food product can be stored refrigerated or unrefrigerated, and remain edible and free from noticeable or harmful degradation or contamination by microorganisms.) As a result, methods and apparatuses suitable for deactivating, i.e., killing or sterilizing, such microorganisms and thereby extending the shelf-life of perishable foods, such as strawberries, oranges, tomatoes, zucchini, apples, and other edible food products, are desirable.

The photobiological effects of light, including infrared light (780 nm to 2600 nm; i.e., $3.9 \times 10^{14}$ Hz to $1.2 \times 10^{14}$ Hz), visible light (380 to 780 nm; i.e., $7.9 \times 10^{14}$ Hz to $3.9 \times 10^{14}$ Hz), near ultraviolet light (300 to 380 nm; i.e., $1.0 \times 10^{15}$ Hz to $7.9 \times 10^{14}$ Hz) and far ultraviolet light (170 to 300 nm; i.e., $1.8 \times 10^{15}$ Hz to $1.0 \times 10^{15}$ Hz), have been studied, and efforts have been made to employ light to deactivate microorganisms on food products or containers for food products. See, e.g., U.S. Pat. Nos. 4,871,559; 4,910,942; and 5,034,235, issued to Dunn et al. (hereinafter, the '559, '942, and '235 patents, respectively), all of which are incorporated herein by reference.

Other studies of the photobiological effects of light are reported in Jagger, J., "Introduction to Research in Ultraviolet Photobiology", Prentice Hall, Inc., 1967. U.S. Pat. No. 2,072,417 describes illuminating substances, e.g., milk, with active rays, such as ultraviolet rays; U.S. Pat. No. 3,817,703 describes sterilization of light-transmissive material using pulsed laser light; and U.S. Pat. No. 3,941,670 describes a method of sterilizing materials, including foodstuffs, by exposing the materials to laser illumination to inactivate microorganisms.

Another attempt to prolong the shelf-life of perishable food products consists of the application of microbiocides and/or microbiostats to the surface of the perishable food products. As used herein, the terms microbicide and microbiostat include substances for killing or preventing the growth/reproduction of microorganisms (as the term microorganisms is defined herein). One example of microbiocides are chemical fungicides. Generally, the microbicide and/or microbiostat :Ls combined with an emulsifying agent and is then applied to the surface of the food product. The emulsifying agent aids in the application and action of the microbicide and/or microbiostat agent, and ensures that the microbicide and/or microbiostat agent remains on the surface of the food product and deactivates microorganisms during shipping until the food product is consumed.

Problematically, such microbiocides and microbiostats have come under increased scrutiny by various governmental agencies, and in some cases have been shown to be potential human carcinogens. As a result, several microbiocides and microbiostats that were once commonly applied to the surface of food products in order to prolong the shelf-life of the food products have been or could be banned by governmental agencies from use with food products. Therefore, an approach to prolonging the shelf-life of perishable food products, that does not require the use of a microbicide or a microbiostat, such as a chemical fungicide, is highly desirable.

The present invention advantageously addresses the above and other needs.

SUMMARY OF THE INVENTION

The present invention advantageously addresses the needs above as well as other needs by providing a device and method for deactivating microorganisms, and more particularly for deactivating microorganisms using short-duration, high-intensity pulses of broad-spectrum polychromatic light.

In one embodiment, the invention can be characterized as an apparatus for deactivating microorganisms that employs a flashlamp; a power supply coupled to the flashlamp; packaging material moving means for moving packaging material relative to the flashlamp in order to sequentially expose portions of the packaging material to high-intensity, short-duration pulses of polychromatic light in a broad spectrum emitted from the flashlamp; a photodiode for detecting the intensity of the high-intensity, short-duration pulses of polychromatic light in a broad spectrum and for generating an output signal indicative of the intensity having been detected; a difference circuit coupled to the photodiode for determining a difference between the output signal and a setpoint signal, the setpoint signal corresponding to a setpoint intensity, and for generating a difference signal indicative of the difference having been determined; and a control circuit, coupled to the difference circuit, for controlling a power level supplied by the power supply to the flashlamp, and for increasing the power level in the event the difference signal indicates that the intensity having been detected has fallen below the setpoint intensity. The apparatus may also include a fiberoptical conductor for conducting at least a portion of the high-intensity, short-duration pulses of polychromatic light in a broad spectrum from a first end of the fiberoptical conductor to a second end of the fiberoptical conductor. The first end of the fiberoptical conductor is positioned to receive the high-intensity, short-duration pulses of polychromatic light in a broad spectrum, and the second end is positioned to direct the high-intensity, short-duration pulses of polychromatic light in a broad spectrum to the photodiode.

In another embodiment, the apparatus includes a fault detection circuit that generates a fault signal in the event the output signal indicates that the intensity having been detected has fallen below a threshold intensity. The control circuit deactivates the apparatus in the event the fault signal indicates that the intensity having been detected has fallen below the threshold intensity.

In a further embodiment, the invention can be characterized as an apparatus for deactivating microorganisms having a flashlamp; packaging material moving means for moving packaging material relative to the flashlamp in order to sequentially expose portions of the packaging material to high-intensity, short-duration pulses of polychromatic light in a broad spectrum emitted from the flashlamp; an outer safety glass surrounding the flashlamp; and an external coating (i.e., a first external coating) applied to first and second ends of the outer safety glass. The external coating may, for example, include Teflon, and/or Platinum. In one variation of this embodiment, a second external coating at least partially covers the first external coating.

In an additional embodiment, the invention can be characterized as an apparatus for deactivating microorganisms using a first flashlamp; a second flashlamp; a fill pipe including, an first portion juxtaposed with the first flashlamp, and a second portion juxtaposed with the second flashlamp. The first portion is positioned to occupy a first side of a packaging material tube, and the first flashlamp is positioned to occupy a second side of the packaging material tube, as the packaging material tube is passed over the first portion and the first flashlamp. The second portion is positioned to occupy the second side of the packaging material tube, and the second flashlamp is positioned to occupy the first side of the packaging material tube, as the packaging material tube is passed over the second portion and the second flashlamp.

In another further embodiment, the invention can be characterized as an apparatus for deactivating microorganisms employing a first linear flashlamp; a first water jacket enveloping the first linear flashlamp; a first cooling water conduit formed between an exterior of the first linear flashlamp and an interior of the first water jacket; a second linear flashlamp; a second water jacket enveloping the second linear flashlamp; a second cooling water conduit formed between an exterior of the second linear flashlamp and an interior of the first water jacket; a fill pipe juxtaposed between the first water jacket and the second water jacket; a sterile air pipe enveloping the fill pipe; a sterile air conduit formed between an exterior of the fill pipe and an interior of the sterile air pipe; a reflector enveloping the sterile air pipe; and an outer safety glass enveloping the first water jacket, the second water jacket, and the reflector.

In an alternative embodiment, the invention can be characterized as an apparatus for deactivating microorganisms with a first linear flashlamp; a second linear flashlamp; a fill pipe interposed between the first linear Elashlamp and the second linear flashlamp; a sterile air pipe enveloping the fill pipe; a sterile air conduit formed between an exterior of the fill pipe and an interior of the sterile air pipe; and an outer safety glass enveloping the first flashlamp, the second flashlamp and the sterile air pipe.

In another additional embodiment, the invention can be characterized as an apparatus for deactivating microorganisms employing a flashlamp; and a first holder including a first lamp holding device. The lamp holding device includes a holding cylinder including a first flange having a first frustioconical surface; a first O-ring juxtaposed against the frustioconical surface; and a first compression cylinder for applying a first force to the first O-ring that compresses the first O-ring against the first frustioconical surface. A first end of the flashlamp is positioned in the holding cylinder and extends past the first flange, and the first frustioconical surface is oriented at a less than ninety degree angle relative to an exterior of the flashlamp. The frustioconical surface, in combination with the first force, causes the first O-ring to compress against the flashlamp so as to form water tight seals between the first O-ring and the first frustioconical surface, and between the first O-ring and the flashlamp.

In yet another embodiment, the invention can be characterized as an apparatus for deactivating microorganism having a U-lamp including a first electrode and a second electrode; means for positioning the U-lamp into a packaging material cup; and a holder device. The holder device includes a first receptacle for receiving the first electrode; a second receptacle for receiving the second electrode; and a lamp holding device positioned in the second receptacle. The lamp holding device is substantially cylindrical in shape, with a distal portion positioned away from the U-lamp and a proximal portion positioned near the U-lamp. The lamp holding device is made from a rigid material and allows the proximal portion to move relative to the distal portion within the second receptacle. A first O-ring is positioned at an exterior of the distal portion between the lamp holding device and the second receptacle; and a second O-ring is positioned at an interior of the proximal portion between the holding device and the U-lamp.

In yet a further embodiment, the invention can be characterized as an apparatus for deactivating microorganisms with a linear flashlamp; a light guide, positioned to receive light emitted from the linear flashlamp; and means for positioning the light guide within a packaging material cup. The light guide, in one variation, is a plurality of bent quartz rods. In another variation, the light guide has a middle layer for directing light toward an interior bottom surface of the packaging material cup; and at least two side layers for directing light toward an interior side surface of the packaging material cup. The side layers of this variation curve away from the middle layer at lower ends.

BRIEF DESCRIPTION OF THE DRAWINGS

The above and other aspects, features and advantages of the present invention will be more apparent from the following more particular description thereof, presented in conjunction with the following drawings wherein:

FIG. 14 is a cross-sectional view of a portion of the other variation of the light assembly shown in FIG. 11;

FIG. 15 is a schematic diagram showing a variation of a fiber optical feedback system useable in the one and the other variations of the light assemblies of FIGS. 8 and 11;

FIG. 19 is a cross-sectional view of a further variation of a light assembly, which may be a part of the other embodiment or the further embodiment of the packaging assembly as shown in FIGS. 3 and 4;

FIG. 20 is a detailed cross-sectional view of a lamp holding device that provides for non-uniformities in U-lamps used in the further variation of the light assembly shown in FIG. 19;

FIG. 21 is another detailed cross-sectional view of the lamp holding device wherein a non-uniform U-lamp has been employed;

Corresponding reference characters indicate corresponding components throughout the several views of the drawings.

DETAILED DESCRIPTION OF THE PREFERRED EMBODIMENTS

The following description of the presently contemplated best mode of practicing the invention is not to be taken in a limiting sense, but is made merely for the purpose of describing the general principles of the invention. The scope of the invention should be determined with reference to the claims.

Figure 1:
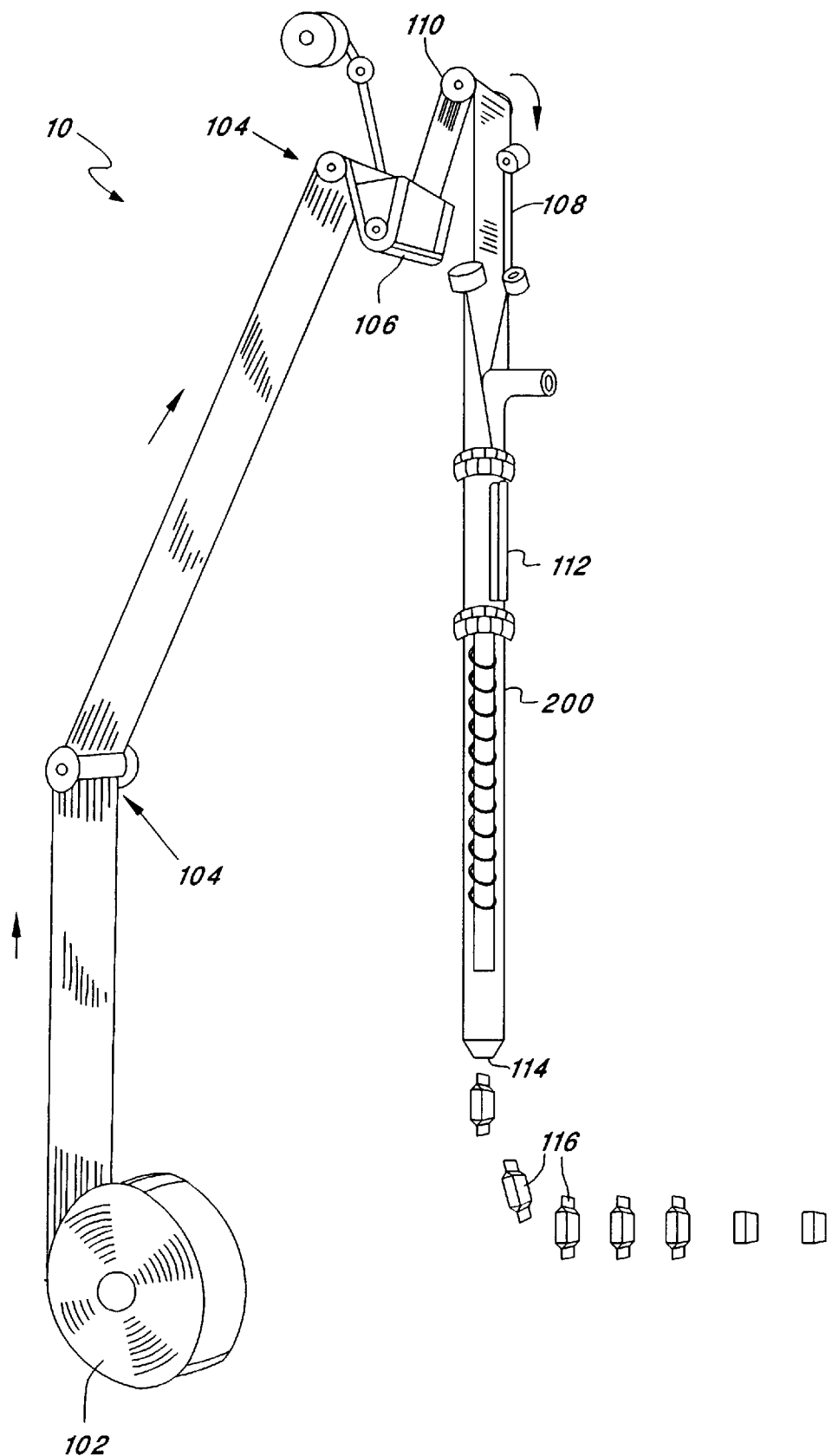
FIG. 1 is a schematic illustration of one embodiment of an aseptic packaging apparatus made in accordance with the present invention, wherein a continuous packaging film is formed into individual packaging units and simultaneously filled with a food product and, wherein microorganisms on the packaging film are deactivated prior to the filling of the individual packaging units using high-intensity (i.e., 0.01 J/cm$^2$ to 50 J/cm$^2$, e.g., 0.5 J/cm$^2$, energy density measured at the surface of the packaging film), short-duration (i.e., 0.001 ms to 100 ms, e.g., 0.3 ms) pulses of polychromatic light in a broad spectrum (i.e., 170 nm to 2600 nm; $1.8 \times 10^{15}$ Hz to $1.2 \times 10^{14}$) to provide aseptically packaged food products.

Referring to FIG. 1, An aseptic packaging apparatus 10 is shown in which a reel of conventional flexible aseptic packaging material 102 is optionally directed by means of a series of rollers 104 in accordance with conventional practice, to a solution of absorption enhancing agent, in a dipping-trough 106. The packaging material may typically comprise a layered structure of one or more internal coating and sealing layers, a metal foil such as aluminum foil, a laminating layer or paper layer and an external layer, in accordance with conventional practice. The internal layer and the external layer may be made from polyethylene. Advantageously, the interior of the packaging material is preferably at least partially reflective of light in a broad spectrum.

Excess absorption enhancing agent solution may be removed by rollers 110, with the film being subsequently formed into a longitudinally sealed tube by a longitudinal sealing apparatus 112. Depending upon whether a lap seal or a fin seal is desired, a strip 108 may be applied to one edge of the packaging material to reinforce the longitudinal seam, and to prevent the product from coming into contact with the edge of the film 102.

An important aspect of aseptic packaging apparatus 10 is a product filling and flashlamp assembly 200 that is described in more detail below in reference to FIG. 2. The aseptic packaging apparatus of FIG. 1 is described in raore detail in the '559 patent previously incorporated by reference.

Figure 2:
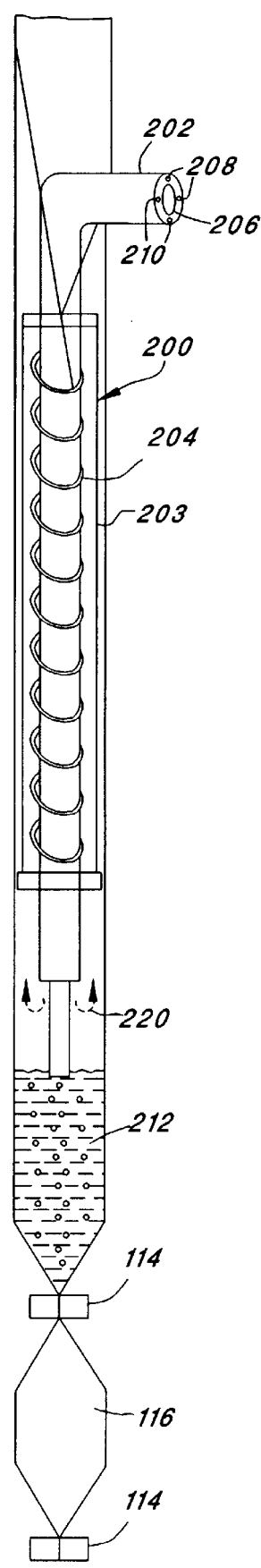
FIG. 2 is a more detailed schematic illustration, partially in section, of a filling and sterilization assembly of the aseptic packaging apparatus of FIG. 1.

Referring next to FIG. 2, a filing and flashlamp assembly 200 is shown. The illustrated flashlamp assembly 200 comprises an outer support tube 202, having attached thereto one or more high power Xenon flashlamps 204 distributed about and along the outer support tube 202 such that upon pulsing, the entire inner surface of the sealed longitudinally sealed tube (or packaging material tube) is subject to high-intensity (i.e., 0.01 J/cm$^2$ to 50 J/cm$^2$, e.g., 0.5 J/cm$^2$, energy density measured at the surface of the packaging film), short-duration (i.e., 0.001 ms to 100 ms, e.g., 0.3 ms), pulses of incoherent, polychromatic light in a broad spectrum (i.e., 170 nm to 2600 nm; 1.8×10$^{15}$ Hz to 1.2×10$^{14}$ Hz). A variety of arrangements of the flashlamps 204 along the outer support tube 202 is feasible, with preferably the entire inner surface of the packaging material tube being exposed to the pulsed light. As shown a helical, or coil-shaped, flashlamp may be utilized, or a plurality, e.g., 2 or 4, of substantially linear flashlamps may be utilized. Preferably, a cylindrical outer safety glass 203 surrounds the flashlamps, protecting the flashlamps 204 from food product splash, ablated contaminants, presterilization agents and the like.

When a plurality of linear flashlamps are utilized, such as shown in several of the FIGS. described below, such flashlamps may all be illuminated simultaneously, may be illuminated in pairs, or may be illuminated serially, in a "Gatling gun" type approach. Preferably, however, the linear flashlamps are illuminated simultaneously, which enables the use of lower fluence levels per flash, while preserving a high overall fluence level and a high degree of packaging material sterilization.

Such lower fluence per flash can be employed when the plurality of linear flashlamps are simultaneously illuminated, because light from adjacent flashlamps cooperates at boundaries between such flashlamps in order to assure that a minimum total fluence is achieved over the entire surface being treated. In contrast, with, for example, the Gatling gun approach, a higher fluence per flash must be used in order to assure that such minimum total fluence is achieved at the boundaries between the flashlamps. Because a lower fluence per flash can thus be used when the flashlamps; are simultaneously illuminated, each flashlamp can be supplied with less energy per flash, thus decreasing flashlamp stress and increasing the useful life of the flashlamps. Also, the size of an energy storage capacitor needed in a power supply for the flashlamps can be, thus, reduced if simultaneous illumination is used, thereby reducing cost and increasing efficiency.

Simultaneous illumination of the flashlamps also reduces the number of switching circuits needed as compared to the number needed to illuminate the flashlamps individually, and reduces the number of simmer power supplies needed to maintain the flashlamps at low current levels between illuminations. Also, simultaneous illumination increases the efficiency of energy transfer between the power supply and the flashlamps because a high voltage may be used (as measured across a series combination of flashlamps).

When a plurality of linear flashlamps are employed and simultaneous illumination of the flashlamps in pairs is desired, such flashlamps may be connected in a series fashion so as to enable pairs of flashlamps to serve respectively as forward and return current paths for one another. By connecting the flashlamps in series, the need to provide a separate insulated return wire (or other return current path) is eliminated, thus further simplifying overall design of the aseptic packaging apparatus and maximizing efficient space utilization within the flashlamp assembly.

Within the outer support tube 202 is a sterile food product tube 206 (or fill pipe 206). Flashlamp electrical cables 208 and optional flashlamp coolant lines 210 may be located intermediate (i.e., between) the outer support and sterile food product tubes 202, 206. In addition, sterile air 220 provided under pressure from a suitable supply (not shown) may be conducted between the outer support and sterile food product tubes 202, 206 for discharge within the packaging material tube. The sterile air 220 may be produced by a variety of techniques including filtration, incineration and/or the use of high-intensity, short-duration pulses of polychromatic light in a broad spectrum, as described herein.

In operation, the longitudinally sealed tube, which is transversely sealed by a suitable transverse sealing apparatus 114 (FIG. 1) has introduced therein a predetermined portion of substantially sterile food product 212. The sterile food product may be produced by short-time, high-temperature processing or by other processes (such as through the application of high-intensity, short-duration pulses of polychromatic light in a broad-spectrum, as described herein). The longitudinally sealed tube is advanced one package length, while the flashlamp assembly 200 is pulsed a plurality of times in order to repeatedly sterilize the entire adjacent interior surface of the longitudinally sealed tube above the food product 212 with high-intensity, short-duration pulses of polychromatic light in a broad spectrum.

Sterile air 220 exits the outer support tube 202 and is carried over the flashlamp assemblies to cool the flashlamps, to remove from the longitudinally sealed tube any ablation products produced by the flashlamp discharge and to prevent contamination from settling on the treated area of the packaging material tube. Following transverse sealing, the packaging material tube may be separated (e.g., cut) into individual consumer packages 116 (see also FIG. 1).

Figure 3:
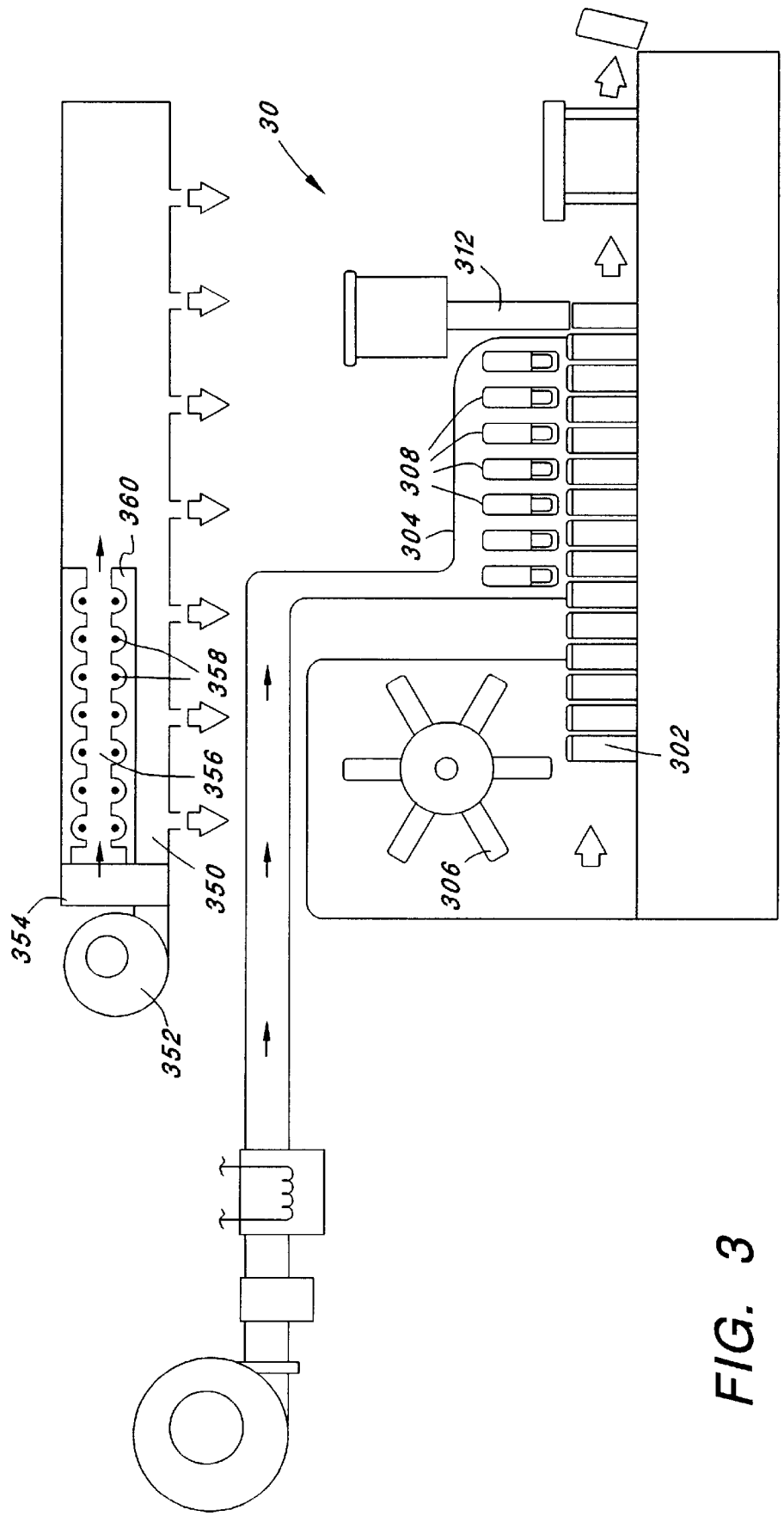
FIG. 3 is a schematic illustration of another embodiment of an aseptic packaging apparatus made in accordance with the present invention wherein a preformed food product containers are filled with a food product, and wherein microorganisms on the inner surface of the preformed food product containers are deactivated prior to the filling of the preformed food product containers using high-intensity, short-duration pulses of polychromatic light in the broad spectrum.

Referring to FIG. 3, the present method may also be applied to other types of aseptic packaging systems, such as those that utilize preformed product containers. Illustrated is one such aseptic packaging apparatus 30. The packaging apparatus 30 utilizes preformed product containers 302 that are introduced into a sterilization zone 304 of the apparatus 30. Optionally an absorption enhancing agent solution, as previously described, may be sprayed into containers 302 by means of a spraying apparatus 306 before the containers are illuminated. Subsequently, the containers progressively pass through a plurality of flashlamp treatment stations 308 in which reciprocating "U"-shaped flashlamps (U-lamps), linear flashlamps, bulb-type flashlamps and/or flashlamps of other configurations are introduced above or into the container openings. The flashlamps are pulsed, i.e., illuminated, at least once per product container 302. The treatment stations 308 are then withdrawn and each product container 302 is advanced by one or more flashlamp treatment stations 308, and the process is repeated so that the entire interior surface of each of the product containers 302 is subjected to one or more high-intensity, short-duration pulses of incoherent polychromatic light in a broad spectrum as it progresses along the treatment stations 308.

A sterile air purge apparatus may also be utilized to remove any material ablated from the interior of the product containers 302, to prevent contamination from settling in the product containers 302 having been treated (or sterilized) and to cool the flashlamps.

Figure 5:
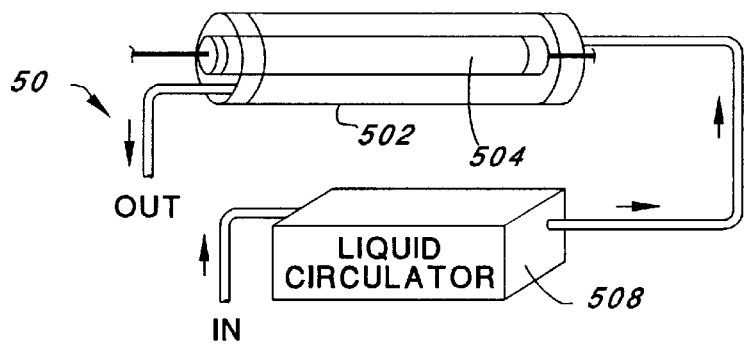
FIG. 5 is a schematic view of an embodiment of a pulsed light processing apparatus that treats pumpable products flowing longitudinally through a jacket surrounding an elongated, incoherent pulsed light source with the high-intensity, short-duration pulses of polychromatic light in the broad spectrum.
Figure 6:
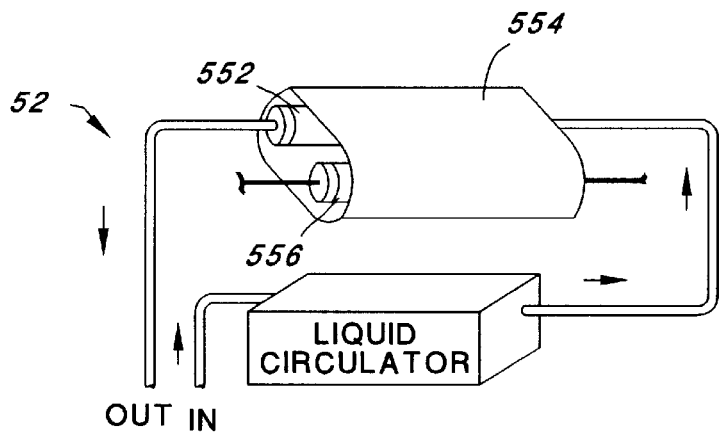
FIG. 6 is a schematic view of another embodiment of the pulsed light processing apparatus of FIG. 5, wherein pumpable food products flowing in a direction parallel to one or more elongated incoherent light sources are treated with the high-intensity, short-duration pulses of polychromatic light in a broad spectrum.

If desired, a suitable stationary battery of flashlamps may also be provided to treat the exterior and edge surfaces of the product containers 302 upon their flowing through the pulsed light treatment zone 356. Thus, a dust particle or bacterial colony forming unit carried by the air or other gasses is treated from all sides and is not self-shielded. Other fluid treatment arrangements, such as shown in FIGS. 5 and 6, may, in other embodiments, be utilized in lieu of or in addition to the gas sterilization apparatus 350 shown.

Figure 4:
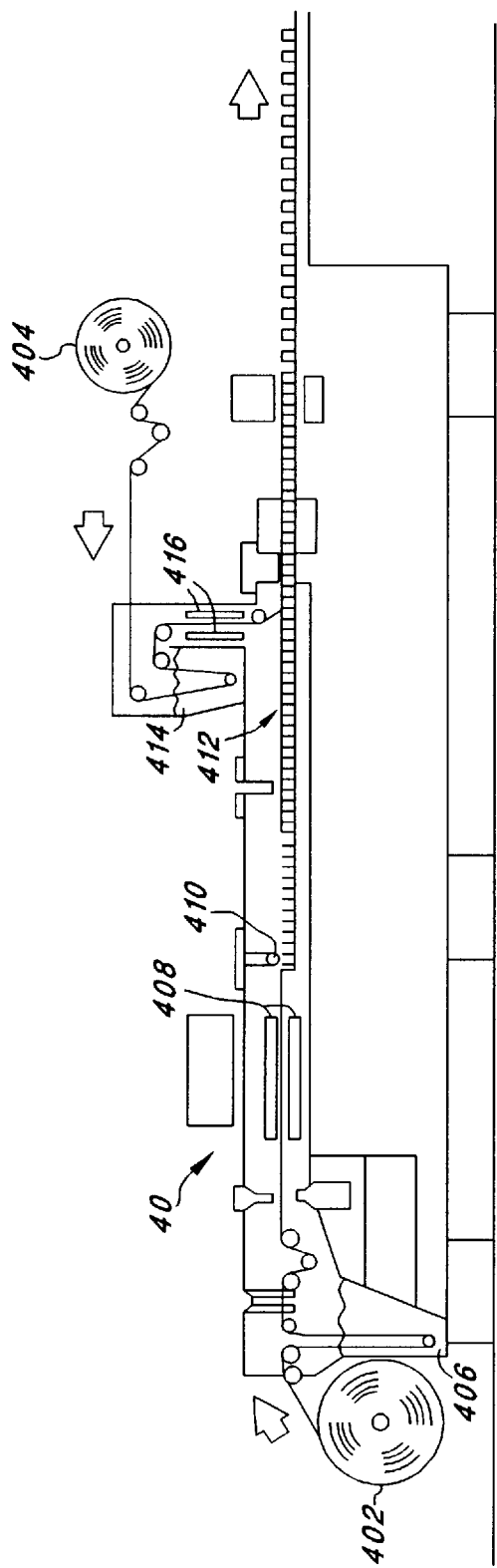
FIG. 4 is a schematic illustration of a further embodiment of an aseptic packaging apparatus that forms food product containers from rolls of thermoplastic and rolls of lid material and then fills the food product containers with a food product, and wherein microorganisms on the inner surface of the preformed food product containers are deactivated prior to the filling of the preformed food product containers using the high-intensity, short-duration pulses of polychromatic light in the broad spectrum.

Illustrated in FIG. 4 is an additional embodiment of an aseptic packaging apparatus 40 that comprises two reels 402, 404 of plastic packaging material, one for a container body of a finished package and one for a package lid. Container body packaging material may be conducted through an optional absorption enhancing agent bath 406, as previously described. Such packaging material 402 may then be conducted through a suction and drier section to remove excess absorption enhancing agent solution.

The container body packaging material is next subjected to high-intensity, short-duration pulses of incoherent polychromatic light in a broad-spectrum by an array 408 of flashlamps extending longitudinally along a direction of travel of the container body packaging material. The container body packaging material 402 may then be thermoformed into suitable containers, such as cups, by a forming apparatus 410, and then filled with a measured amount of an aseptically processed food product at a filling station 412.

The lid packaging material may similarly be passed through an absorption enhancing agent bath 414, subjected to a plurality of high-intensity, short-duration pulses of polychromatic light in a broad-spectrum by a flashlamp array 416. The lid packaging material is then used to seal the filled, formed containers. The entire apparatus may be maintained under passage through the treatment zone. The product containers 302, having been sterilized, pass through a filling station 312 where a measured amount of preprocessed food product is introduced into each product container 302. Each product container 302 is then sealed at the top with a sterile lid using conventional sealing methods.

A laminar, sterile air curtain may be provided over the entire aseptic packaging apparatus 30 in order to prevent reinfection (i.e., recontamination with microorganisms) of the product containers 302. The sterile air may be provided by a gas sterilization apparatus 350, which includes an air input blower 352, that pumps air through a filter 354 to a pulsed light treatment zone 356 containing a bank of high power Xenon flashlamps 358 enclosed in a reflective housing 360. The air is continuously forced through the treatment zone 356 at a rate that, in conjunction a pulse repetition rate of the flashlamps 358, insures that all of the air is subjected to a plurality of high-intensity, short-duration pulses of incoherent polychromatic light in a broad-spectrum, as previously described, as the air passes through the pulsed light treatment zone 356.

Preferably, in accordance with the present embodiment, the pulses of light will be UV-rich (e.g., having at least 5 percent of the light energy at wavelengths between 170 and 380 nanometers) and desirably has an energy density of at least 0.1 joules per square centimeter, e.g., at least 0.4 or 0.5 $J/cm^2$ throughout the pulsed light treatment zone 356. Pulse duration may typically be in the range of from about 0.1 to 3 milliseconds, e.g., 0.3 milliseconds.

A muiltiple-lamp reflector array, which is part of the reflective housing 360, provides multidirectional, substantially-even illumination to the air or other gases a sterile air blanket, so as to minimize the possibility of re-contamination.

Referring to FIG. 5, a schematic view is shown of an embodiment of an apparatus for the treatment of pumpable products, such as water, liquid or semi-liquid food products, such as fruit juices or soups, or gasses, such as air, with high-intensity, short-duration pulses of polychromatic light in a broad-spectrum. The apparatus 50 comprises a reflective, cylindrical enclosure defining a treatment chamber 502 through which the product flows and that surrounds a pulsed light source 504 in the embodiment shown, the pulsed light source is a high powered Xenon flashlamp provided with a suitable power source (not shown) in accordance with conventional practice for flashlamp operation.

A liquid circulation pump 508 controls the flow rate of the product through the treatment chamber 502 in relation to the pulse repetition rate of the pulsed light source 504 so that during the product residence time within the treatment chamber 502, all of the product that passes therethrough is exposed to a predetermined number of high-intensity, short-duration pulses of incoherent polychromatic light in a broad-spectrum. The product exiting the treatment chamber 502 is therefore sterile (or disinfected) to a desired degree.

In some embodiments, the product treatment chamber 502 is arranged so as to be separate from the pulsed light source 504, preventing the product from contacting the light source 504.

Such may be achieved, for example, by employing a quartz jacket (or quartz cylinder) around the light source 504 with the product passing outside the quartz jacket. Advantageously, cooling water may be circulated between the light source 504 and the quartz jacket.

The diameter of the treatment chamber will vary depending upon many factors including but not limited to the specific absorption characteristics of the product to be treated, the physical and operating characteristics of the light source 504, i.e., flashlamps, and the degree of product mixing between pulses, i.e., flashes, of light. The treatment chamber 502 may include a reflector assembly as its outer wall or as an external reflector, in order to reflect illumination traversing the product back in toward the product. When an external reflector is used, the reflector assembly may include a quartz cylinder (or quartz tube) inside which the product is circulated and outside which the external reflector is positioned.

It is noted that fluids such as air and water are relatively transparent to light, including significant portions of the UV spectrum. Accordingly, there is relatively little attenuation through absorption in such media, with the flux density decreasing largely only as a function of distance from the light source. However, for fluids that have significant absorption, flux density will decrease as a function both of distance from the flashlamp and of product absorption. In any event, the desired minimum flux density, e.g., 0.4 or 0.5 $J/cm^2$ (or even as low as 0.1 or 0.2 $J/cm^2$ depending on the particular microorganisms to be deactivated), should be maintained throughout the treatment zone.

Alternatively or in addition, mixing must occur to insure that all of the fluid being treated is subjected to an appropriate flux intensity and number of pulses (for the desired degree, or level, of deactivation, i.e., kill or sterilization).

Referring to FIG. 6, while the flashlamp 504 (FIG. 5) is located internally of the treatment chamber 502 (FIG. 5) in the apparatus 50 of FIG. 5, one or more flashlamps 556 may alternatively (or in addition) be located externally of the treatment chamber 552. A preferred design is shown in which product to be treated is conducted through a treatment chamber 552 employing transparent treatment conduit (e.g., a quartz tube) 552. The treatment chamber 552 is positioned along one focus of an elliptical reflector 554. A flashlamp 556 is positioned along another focus of the elliptical reflector 554.

In a variation of the embodiment shown, multiple elliptical reflectors, each having a flashlamp at one focus and the treatment chamber 552 (which in the present variation is elongated) at the other focus (not shown), may be utilized if desired.

Referring again to the variation shown, the flashlamp 556 may be jacketed in a quartz cylinder (or tube) for water cooling and/or liquid spectral filtering, in a manner similar to that described above in reference to the above-described embodiments. In this manner, because the light pulses are focused by the elliptical reflector toward the center of the treatment chamber 552, compensation is provided for the light absorption of the liquid being treated, so that all of the liquid is subjected to more uniform light treatment.

Figure 7:
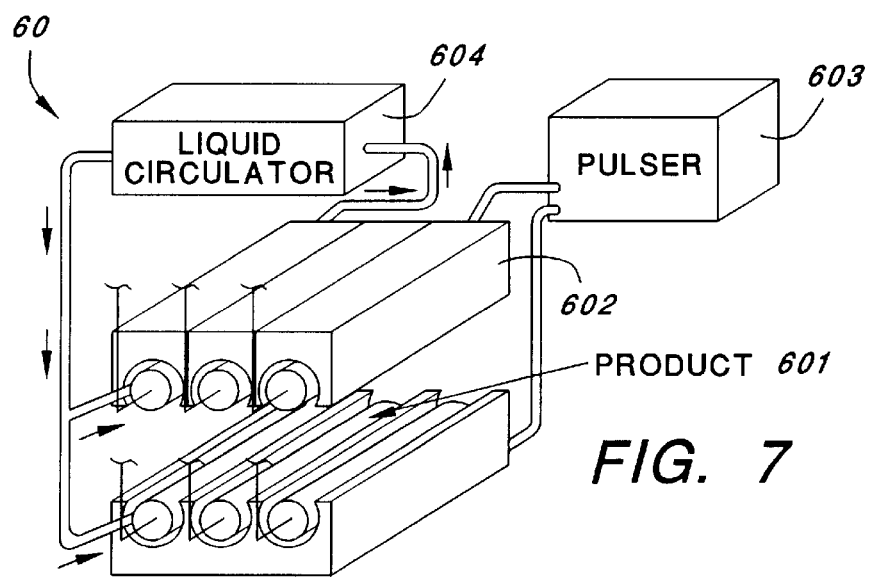
FIG. 7 is a schematic view of a further embodiment of a pulsed light processing apparatus for treating products with the high-intensity, short-duration pulses of polychromatic light in the broad spectrum as such products pass through a treatment station or zone.

Referring to FIG. 7, an embodiment is shown of a light processing station 60 comprising a pulsed light source/reflector array 602 through which a product 601 to be treated passes, falls or tumbles. The pulsed light source/reflector array 602 is connected by umbilicals to an electrical pulse forming network 603 that energizes the pulsed light source/reflector array 602 either simultaneously or sequentially, and a cooling/filtering liquid circulator 604 that circulates a liquid medium, such as water, through a quartz cylinder external to each flashlamp in the source/reflector array 602 for cooling and/or spectral filtering by the use of selected liquid solutions with desired spectral transmittance/absorbance characteristics.

The pulsed light source/reflector array 602 uses a plurality of flashlamps and associated reflectors to create a high-intensity, short-duration pulses of incoherent polychromatic light in a broad spectrum in a treatment region in which the products to be treated are exposed to the high-intensity, short-duration pulses of polychromatic light in a broad spectrum. While the illustrated embodiment 60 uses straight (i.e., linear or cylindrical) flashlamps and reflector elements, other arrangements may be utilized. For example, the flashlamps may be constructed in nearly any shape in much the same way that neon lighting signs may be made to nearly any shape. Similarly, the reflectors may be made of many different materials in many different geometries to direct pulses of light from the flashlamps to the product to be treated. "The Optical Design of Reflectors", Second Edition, William B. Elmer, Published by John Wiley and Sons, Inc., New York is an introduction to the fundamentals of reflector design.

Although the present embodiment includes many potential applications for the reduction of viable organism, microbe or virus numbers, or enzymatic activity in the preservation of food products, the methods employing high-intensity, short-duration, broad-spectrum, polychromatic, incoherent pulses of light for the sterilization of water and packaging materials in aseptic packaging methods are a particularly useful aspect of the embodiments described herein. In such methods, generally, broad-spectrum flashlamp output, including near and far ultraviolet light components of the spectrum, is normally be employed so that relatively low fluences may be utilized. For example, even at very high organism densities (up to $1\times10^6$ to $1\times10^8$), only one or two flashes al an energy density of 0.4 or 0.5 $J/cm^2$ per flash (or as low as 0.1 $J/cm^2$, or even as low as 0.01 $J/cm^2$ or less, depending on the microorganisms to be deactivated) will result in deactivation, i.e., kill or sterilization, of spores, vegetative bacteria, viruses and the like.

Figure 8:
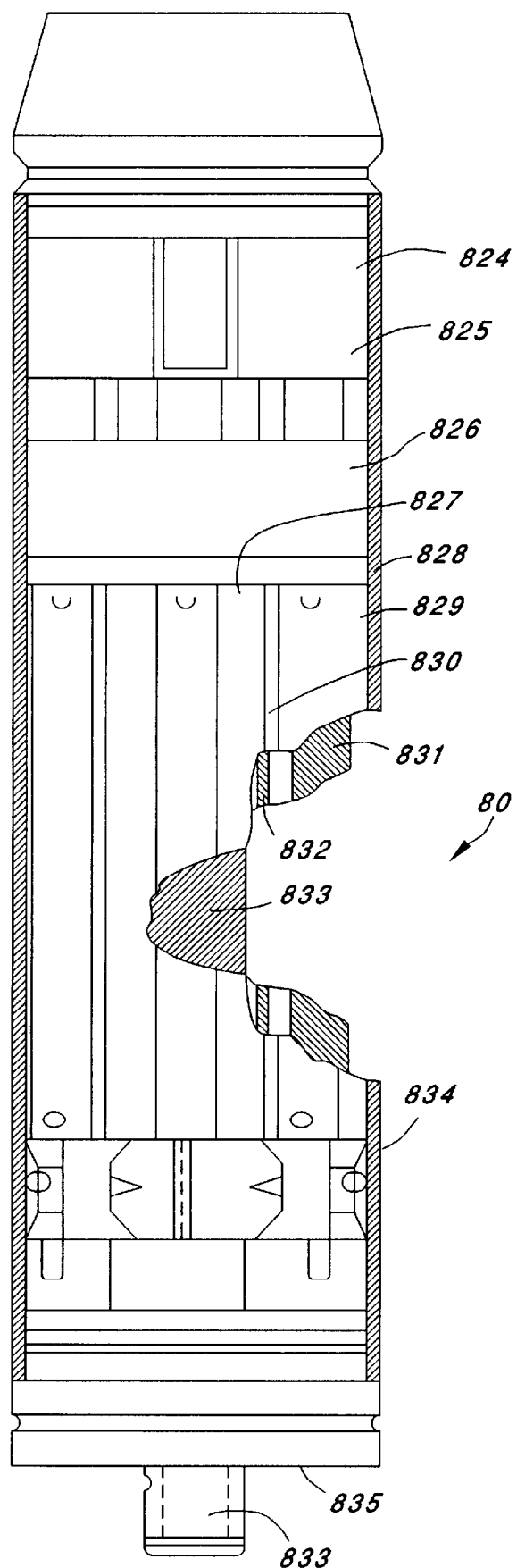
FIG. 8 is a cross-sectional view, partially cut away, of one variation of a light assembly, which may be a part of the filling and sterilization assembly of FIG. 2.

Referring to FIG. 8, shown is a crosssectional view of one variation of a light assembly 80 that may be a part of the filling and sterilization assembly 200 of FIG. 2. A food product tube 833 (or fill pipe 833), is surrounded by an outer support tube 832 (or sterile air pipe 832) that conveys sterile air down to a jet diverter outlet 835. A plurality of flashlamps 831, e.g., 2 or 4, are positioned around a reflector 832, which in some embodiments also serves as the sterile air pipe 832.

The flashlamps 831 are secured in a terminal block 826, which also functions as a highvoltage insulator, coolant water distributor, and anchorage device for the flashlamps 831, a fiber-optical conductor (not shown) and coolant water pipes 210 (or coolant lines 210) (see FIG. 2).

Each of the flashlamps 831 is surrounded by a quartz tube 829 (or water jacket 829). Cooling water is flowed between each of the water jackets 829 and their respective flashlamps 831. Advantageously, the cooling water also serves as a current path for an initial "trigger" for the flashlamps 831, thus optimizing usage of space. The initial trigger provides a capacitance to ground that is used, as is known in the art, to facilitate the initiation of an initial pulse of light from the flashlamp. (In lieu of the cooling water, an electrical wire has heretofore been wrapped in a helical coil around the flashlamp and the "trigger" has been the electrical wire instead of the cooling water. Use of the helical electrical wire as a "trigger" is well known in the art.) The cooling water enters each water jacket 829 through the coolant lines 210 (see FIG. 2).

A quartz safety glass 828 surrounds all of the flashlamps 831, the sterile air pipe/reflector 832, and the fill pipe 833. The outer safety glass 828 serves to protect the flashlamps 831 and the reflector 832 from food product splash, and from presterilization agents that may have been applied to an interior surface of a packaging material tube being decontaminated (or treated).

In addition, the outer safety glass 828 filters out light wavelengths shorter than about 200 nm, which wavelengths could cause the formation of ozone outside the outer safety glass 828 within the packaging material tube. The space within the outer safety glass 828 is preferably filled with Nitrogen gas so as to prevent ozone formation within such space, which ozone could oxidize the sterile air pipe/ reflector 832.

Advantageously, the present embodiment provides fiberoptic conductors (not shown) with respective ends of the fiberoptic conductors positioned near each of the flashlamps 831. within the outer safety glass 828 so as to receive light directly therefrom. Alternatively the fiberoptic conductors may be positioned as shown in FIG. 14, as described below.

The fiberoptic conductors conduct light from within the flashlamp assembly 80, through the space between the fill pipe 833 and the sterile air pipe 832, to a pair of UV-sensitive photodiodes (not shown). The UV-sensitive diodes are placed in a light-screened box (not shown) external to the light assembly 80. Preferably, a neutral density filter, and a UV-selective filter, interposed between the fiberoptical conductor and the UV-sensitive diodes, are used to attenuate the light and to filter off wavelength outside the ultraviolet range, respectively. An output signal from the UV-sensitive photodiodes is passed to a sample and hold circuit (not shown), which is monitored by a control unit (not shown) after each discharge, i.e., flash of light. If the amplitude of the output signal, which is proportional to the peak intensity (during each flash) of the light carried by the fiberoptic conductors, is less than a prescribed minimum amplitude needed to deactivate microorganisms (e.g., 80% of the peak amplitude generated in response to light from new flashlamps) on any given discharge of the flashlamps 831, the control unit may immediately discontinue operation of the packaging material tube until remedial action and resterilization of the light assembly 80 can take place.

Further description of the fiberoptic conductors, the UV-sensitive photodiodes, and the control unit is made below in reference to FIGS. 14 and 15.

Figure 9:
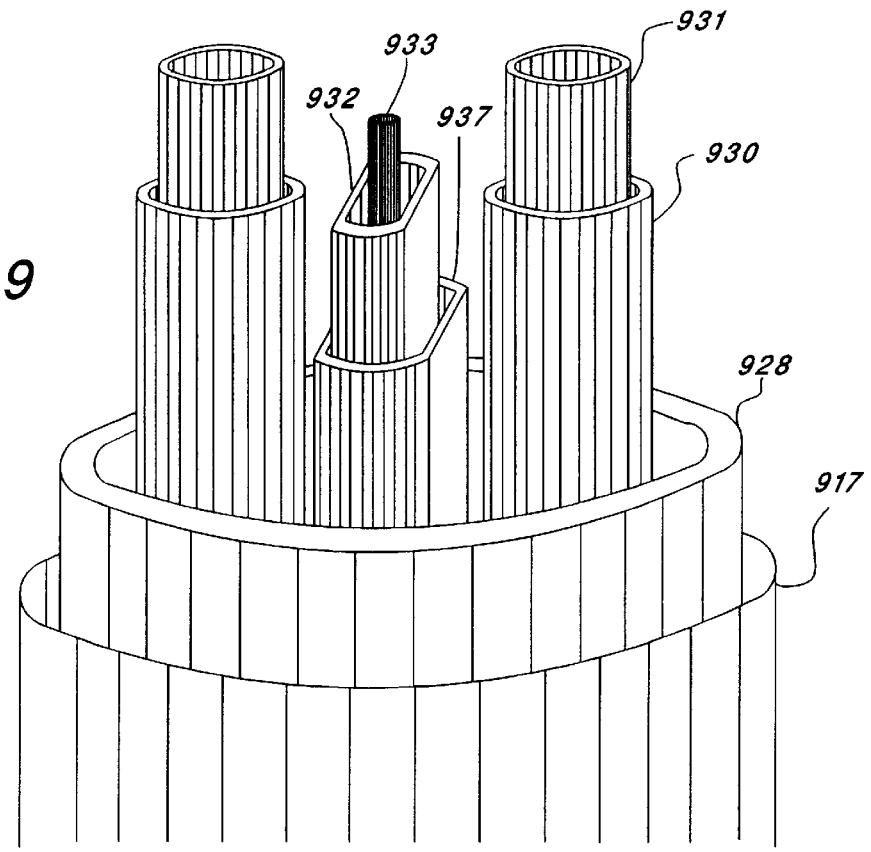
FIG. 9 is a cut away view of one variation of a portion of the light assembly of FIG. 8.

Referring to FIG. 9, shown is a cut-away view of an interior geometry useable with the flashlamp assembly 80 of FIG. 8. Shown is the outer safety glass 928, the flashlamps 931, the water jackets 930, the reflector 937, the fill pipe 933, the sterile air pipe 932 (which in the embodiment of FIG. 9 is separate from the reflector 937) and a packaging material tube 917.

As described above in reference to FIG. 8, a food product to be packaged is transported through the fill pipe 933 to a filing zone (i.e., a portion of the aseptic packaging apparatus, just below the flashlamp assembly, at which food product is introduced into the packaging material tube) (not shown). The fill pipe 933 is surrounded by the sterile air pipe 932, which serves to convey sterile air down to the jet diverter air outlet 835 (see FIG. 8).

The sterile air serves to maintain a positive pressure inside the packaging material tube 917, so that an aseptic environment around and above the flashlamp assembly 80 of FIG. 8 may be sustained when the packaging apparatus is operating, or when it is stopped. The sterile air also cools the outer safety glass 928, which is advantageous given that a portion of the light emitted from the flashlamps 931 is absorbed in the outer safety glass 928, thus causing heating of the outer safety glass 928. The sterile air pipe 932 can also be used as a conveyor for a presterilization agent when the aseptic packaging apparatus is to be sterilized prior to use.

The sterile air pipe 932, is surrounded by the reflector 937, which is treated with or made from reflective agents such that a high degree of reflection is achieved for light wavelengths between 200 nm and 1200 nm. Preferably, the reflector is a sleeve of Teflon-based material marketed under the trade name SPECTRALON, by Labsphere, Inc., of New Hampshire, as described in U.S. Pat. No. 4,912,720, to Springsteen, for LASER CAVITY MATERIAL, issued Mar. 27, 1990, incorporated herein by reference. The reflector 937 is preferably of such geometric design that a uniform light distribution is achieved on an inner surface of the packaging material tube 917.

Advantageously, the reflector 937, if conductive, may also function as a ground lead, or return current path, for the flashlamps 931, which saves space within the assembly 80 (See FIG. 8). (Alternatively, however, when pairs of the flashlamps are connected in a series fashion, the pairs of flashlamps may provide a return current path for each other, thus eliminating the need for a ground lead.) In the embodiment shown, the flashlamps 931 are one or more in number, e.g., two or four, and are gas discharge lamps, such as 230 mm O-ring-mounted lamps such as are available as Part No. 01812-525 from PurePulse Technologies, Inc. of San Diego, Calif. The flashlamps 31 are positioned around the reflector 937 and are secured in the terminal block 826 (see FIG. 8), which functions as an insulator for high voltage, a coolant water distributor and as an anchorage device for the flashlamps 931, fiberoptic conductor, and water jackets 930. As shown, the flashlamps 931 are surrounded by the water jackets 930, and a space is created between the water jackets 930 and the flashlamps 931 through which water is flowed in order to cool the flashlamps 931, and thereby extend the service life of the flashlamps 931. The reflector 937 is cooled by water that is flowed within a space between the reflector 937 and the sterile air pipe 932.

The flashlamp assembly 80 is surrounded by the outer safety glass 928, which, as described above, is made of quartz. As mentioned above, the purpose of the outer safety glass 928 is to protect the flashlamps 931 and reflector 937 from product splash and from the presterilization agent.

Furthermore, the outer safety glass 928 filters off light wavelengths shorter than 200 nm so that no ozone can be created between the outer safety glass and the packaging material tube 917. The space inside the outer safety glass 928, between the outer safety glass 928, and the reflector 937 and water jackets 930 is filled with Nitrogen gas to prevent ozone formation in such space, which could otherwise cause the reflector 937 to become oxidized.

Figure 10:
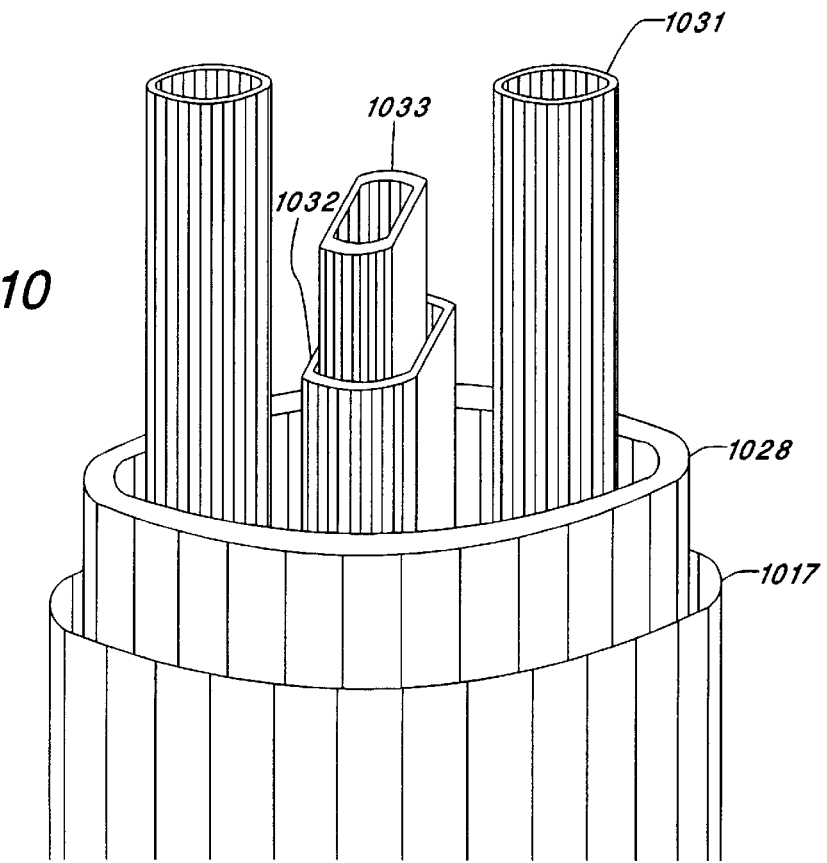
FIG. 10 is a cut away view of another variation of the portion of the light assembly of FIG. 8.

Referring to FIG. 10, a cut-away view of a variation of the portion of the light assembly of FIG. 8 is shown, wherein space optimization features have been employed in accordance with aspects of the present invention in order to achieve optimal space utilization, thereby enabling the usage of the present variation with packaging material tubes of smaller diameters than has otherwise been possible. Shown are the flashlamps 1031, the fill pipe 1033, the sterile air pipe 1032, the outer safety glass 1028, and the packaging material tube 1017. Note that the reflector 937 (FIG. 9), and the water jackets 930 (FIG. 9) are omitted from the variation of FIG. 10.

An outer surface of the sterile air pipe 1032 is treated with a reflective agent (i.e., is reflectorized) so as to achieve a high reflection of light emitted from the flashlamps 31 in the region of between 200 nm and 1200 nm wavelength. Preferably, such reflective agent is the Teflon-based material marketed under the trade name SPECTRALON, as described in the '720 Patent, as mentioned above. Advantageously, by coating the sterile air pipe 1032 with such reflective agent, the need for a separate reflector 937 (such as in the variation of FIG. 9) is eliminated.

Cooling of the sterile air pipe 1032, which also serves as the reflector, and of the flashlamps 1031 is achieved by flowing water in a space within the outer safety glass 1028, outside the flashlamps 1031 and the sterile air pipe, thus eliminating the need for the water jackets 930 (FIG. 9). If the reflective agent on the sterile air pipe 1032 is metallic, it can be coated with a thick layer of silicon oxide in order to protect the reflective agent against the corrosive effects of the water.

Figure 11:
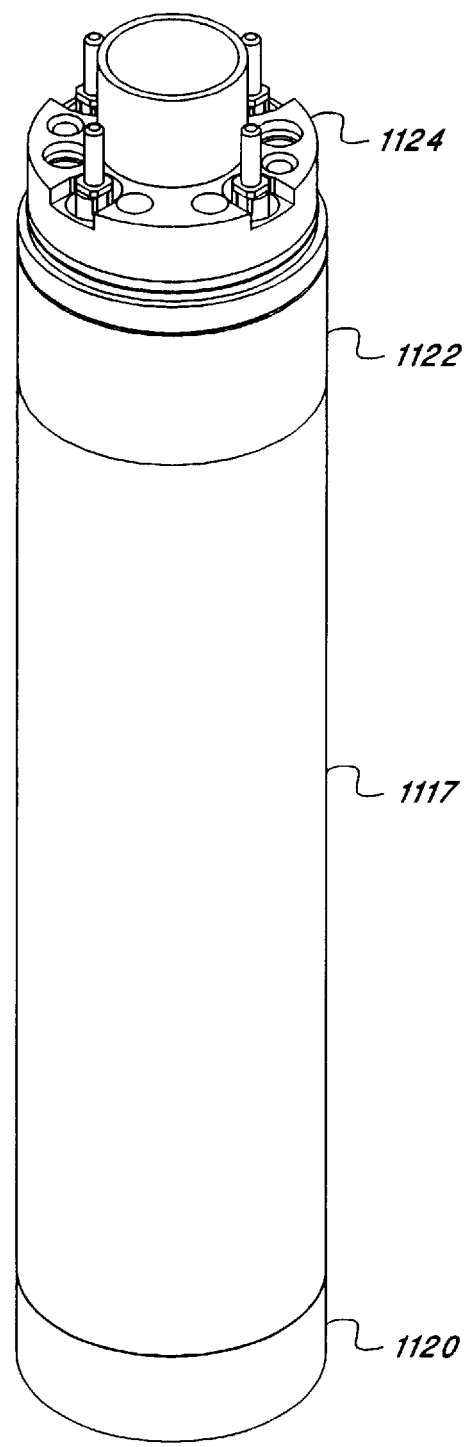
FIG. 11 is a side view of another variation of the light assembly, which may be a part of the filing and sterilization assembly of FIG. 2.

Referring to FIG. 11, a side view is shown of another variation of the light assembly of FIG. 8. The outer safety glass 1117 is shown, along with a lower holder 1120 and first and second upper holders 1122, 1124.

As in the variations shown in FIGS. 8, 9 and 10, the outer safety glass 1117 serves to protect the flashlamps (not shown), the reflector (not shown), the water jackets (not shown), and other structures contained within the light assembly from product splash and presterilization agents.

Figure 12:
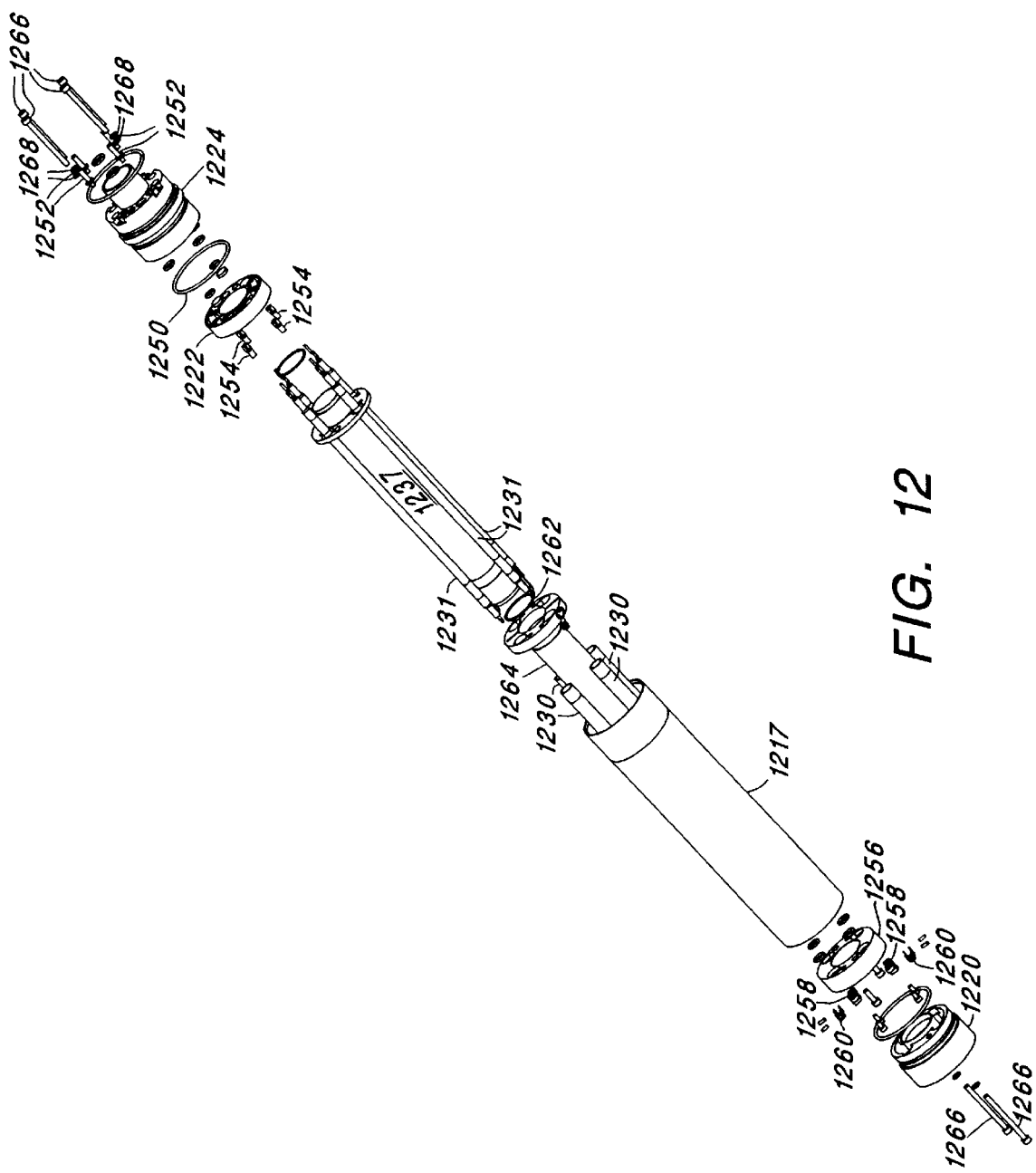
FIG. 12 is a detailed assembly view of the other variation of the light-assembly shown in FIG. 11.

Referring to FIG. 12, a detailed exploded view is shown of the variation of the light assembly of FIG. 11. Shown are the outer safety glass 1217, the flashlamps 1231, the reflector 1237, the water jackets 1230, the lower holder 1220, the first and second upper holders 1222, 1224, a quartz window 1250, a connector 1252, a crimp sleeve 1254, another lower holder 1256, a contact hose 1258, a pusher 1260, a flange 1262, a reflector sleeve 1264, assembly screws 1266, and U-seals 1268.

Assembly of the above-recited components is as shown in FIG. 12, as will be appreciated by one of skill in the art. The outer safety glass 1217 is preferably made from quartz; the flashlamps 1231 may be linear (or cylindrical) flashlamps such as 230 mm O-ring-mounted lamps such as are available as Part No. 01812-525, from PurePulse Technologies of San Diego, Calif.; the reflector 1237 and reflector sleeve 1264 are preferably a stainless steel pipe externally enveloped by a sleeve of Teflon-based material, such as is marketed under the trade name SPEICTRALON, as described in the '720 patent; the water jackets 1230 are preferably quartz cylinders sized to accommodate the flashlamps 1231 and to provide a space thereinbetween through which cooling water may be flowed (or circulated); and the one and the other lower holders 1220, 1256 and the first and second upper holders 1222 are preferably made from 25% glass-loaded Teflon.

The outer safety glass 1217, the flashlamps 1231, the reflector 1237, and the water jackets 1230 function as described above in reference to FIGS. 9 and 10, inter alia. Note, however, that it is a feature of the variation shown to employ the space between the reflector 1237 and water jackets 1230, and the outer safety glass 1217, of FIG. 12, as a return path for cooling water flowed between the water jackets 1230 and the flashlamps 1231. For example, the cooling water may flow down, as oriented in FIG. 12, via the spaces between the flashlamps 1231 and the water jackets 1230, and may return by flowing up through the space between the water jackets 1230 and reflector 1237, and the outer safety glass 1217.

Figure 13:
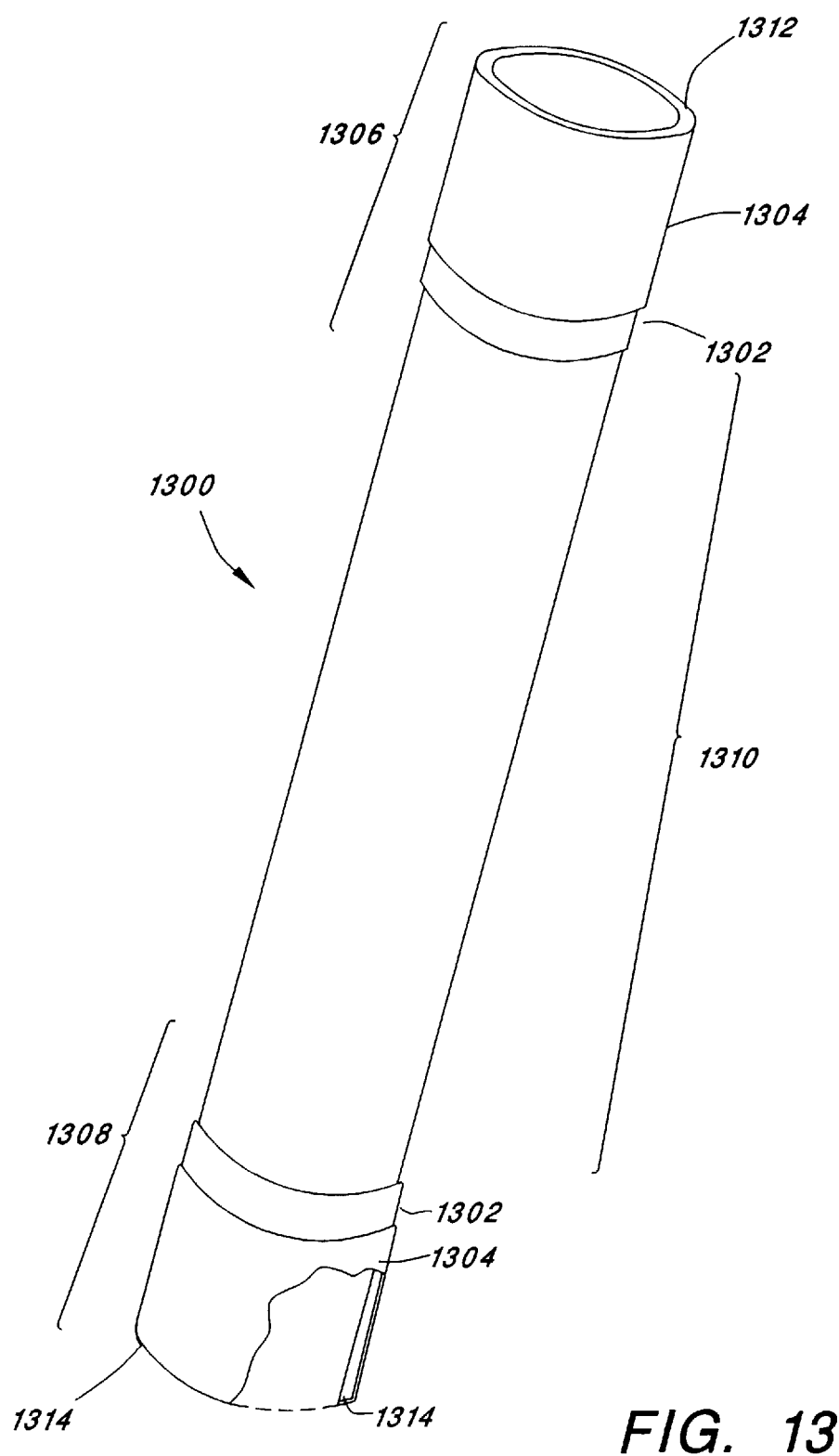
FIG. 13 is a perspective view, partially in section, of an outer safety glass useable in the variation of the light assembly of FIG. 12.

Referring to FIG. 13, a perspective view is shown, partially in section, of the outer safety glass useable in the variation of the light assembly of FIG. 12. Shown is the outer safety glass 1300, which is made from quartz glass, having a first exterior coating 1302 of platinum, and a second exterior coating 1304, outside the first exterior coating 1302, made from Teflon. The first and second exterior coatings 1302, 1304 cover the exterior of the outer safety glass 1300 over end portions 1306, 1308 of the outer safety glass 1300, leaving a center portion 1310 of the outer safety glass 1300 transparent and exposed, and therefore able to conduct light emitted from the flashlamp (not shown) enveloped therein.

The outer safety glass 1300 is held in place by the upper and lower holders (see FIGS. 12 and 13). Gaskets (see FIG. 14) are interposed between the upper and lower holders, and interiors of respective end portions 1306, 1308 of the outer safety glass 1300. The gaskets form a water tight seal between the respective end portions 1306, 1308, thereby allowing the cooling water to be conducted from the upper holder (or lower holder) to the lower holder (or upper holder) via the outer safety glass 1300 in order to effect return of cooling water from the flashlamp, and possibly spectral filtration, as described herein.

Advantageously, the first and second external coatings 1302, 1304 prevent light from passing through the end portions 1306, 1308 of the outer safety glass 1300, i.e., at least one of the first and second external coatings 1302, 1304 is substantially opaque. As a result, light emitted from the flashlamp, and reflected back toward the flashlamp and down (or up) toward the respective gasket by the packaging material tube, cannot penetrate the respective end portions 1306, 1308 of the outer safety glass 1300. Thus, the reflected light is prevented from being reflected onto the gaskets, which, because the light would cause breakdown of polymers in the gaskets, extends the useful life of the gaskets, and helps to minimize down time of the aseptic packaging apparatus.

A further advantage of employing the first and second exterior coatings 1302, 1304 is that they help to prevent chipping or cracking of the end portions of the outer safety glass 1300 during handling.

In order to further enhance these advantageous aspects of the first and second exterior coatings 1302, 1304, such coatings are advantageously lap over respective lower and upper edges 1312, 1314 of the end portions 1306, 1308. In the embodiment shown however, the first and second exterior coatings do not wrap around the upper and lower edges 1312, 1314 of the end portions 1306, 1308 onto any of the interior of the upper and lower end portions 1306, 1308.

Application of the first exterior coating 1302, i.e., the Platinum, is preferably achieved using thermo-chemical deposition processes such as are known in the art, to achieve a thickness of 2000 to 3000 angstroms. Application of the second exterior coating 1300, i.e., the Teflon coating, is preferably achieved using electrostatic processes, such as are known in the art, to achieve an approximate thickness of 0.010 inches.

The second exterior coating 1304 is preferably applied in layers from a powered or granular form, using, e.g., PF8 Teflon powder, and is spray painted or died white during such application. As suggested above, the layers are applied electrostatically and are then scintered after application in order to bond such layers to the outer safety glass and/or to earlier-applied layers of the second exterior coating 1304.

It is noted that the first exterior coating 1302, i.e., the Platinum, both helps the second exterior coating 1304, i.e., the Teflon, to adhere to the outer safety glass 1300, and causes the end portions 1306, 1308 to be in compression, which strengthens the end portions 1306, 1308. the second exterior coating 1304 accounts most of the reflection of light away from the end portions. In alternative variations of the present embodiment, either one of the first or second exterior coatings 1302, 1304 may be omitted, thus employing only the first exterior coating 1302 or the second exterior coating 1304.

In a further variation of the present embodiment, it may also be desirable to coat end portions of the water jackets in a manner similar to that described above with respect to the outer safety glass.

Referring to FIG. 14, a schematic diagram is shown of a detailed cross-sectional view of a portion of the variation of the light assembly shown in FIGS 11 and 12. Shown are the outer safety glass 1417, the flashlamps 1431, the first upper holder 1420, the second upper holder 1458, the fill pipe 1437, and the reflector 1431. Also shown are a pair of flashlamp O-rings 1431 and an outer safety glass O-ring 1452.

The flashlamp O-rings 1450 and the outer safety glass O-ring 1452 are used to form a seal between the upper holders 1458, 1420, and the flashlamps 1431 and outer safety glass 1417, respectively. Ends 1460 of the flashlamps 1431 are positioned in the second upper holder 1458, and electrical connections 1454 are made between the flashlamps 1431 and an appropriate power supply (not shown). The fill pipe 1437 is preferably covered with a sheath of Teflon-based material 1456, marketed under the tradename SPECTRALON, and described in the '720 patent, previously incorporated herein by reference.

Also shown are the water jackets 1459 and the first and second exterior coating 1464, 1466; which are as described in further detail above. As will be appreciated by the skilled artisan, the first and second exterior coating 1464, 1466 shield the outer safety glass O-ring 1452 from any light reflected back toward the outer safety glass 1417 by, for example, the packaging material tube and 917 and 1017 (FIGS. 9 and 10).

Referring to FIG. 15, a schematic diagram is shown of a variation of a fiber-optical feedback system usable in the variations of the light assemblies of FIGS. 8 and 11. Shown are the outer safety glass 1528, the packaging material tube 1517, the water jacket 1529, and the flashlamp 1531. Also shown is a light ray 1550 emanating from. the flashlamp 1531, passing through the quartz water jacket 1529, and outer safety glass 1528 to impinge upon the inner surface 1552 of the packaging material tube 1517.

Reflected from the inner surface 1552 of the packaging material tube 1517 is a first reflected ray of light 1554. A notch 1556 is shown cut into an inner surface 1558 of the outer safety glass 1528. The notch 1556 is a normal right triangle in cross-section and allows the ray of light 1550 to freely pass from inside the outer safety glass 1528 to outside the outer safety glass 1528.

The first reflected ray of light 1554, however, is diverted by an upper surface 1560 of the notch 1556. As a result, a second reflected ray of light 1562 is directed upwards within the outer safety glass 1528 along a trajectory parallel to a central axis (not shown) of the outer safety glass 1528, which is preferably cylindrical. At an upper end 1564 of the outer safety glass 1528, the second reflected ray of light 1562 is captured by a fiber optical conductor 1566 and directed through the fiber optical conductor 1566 from a first end 1568 of the fiber optical conductor 1566 to a second end 1570 of the fiber optical conductor 1566. Upon emerging from the second end 1570, a redirected ray of light 1572 is directed into a UV-sensitive diode 1574. Before reaching the UV-sensitive diode, the redirected ray of light 1572, may pass through a neutral density filter 1580 and/or a "bandpass" filter 1582 that allows light in the UV spectrum to pass, but blocks light outside the UV spectrum.

The UV-sensitive diode 1574 is coupled to a detector circuit 1576 that provides an output indicative of the amount of light impinging upon the UV-sensitive diode 1574. The detector circuit 1576 may include a sample-and-hold circuit, in which case the output is indicative of the peak amount of light impinging upon the UV-sensitive diode 1574 during each flash (with the sample-and-hold circuit being reset prior to each flash). This amount of light, in turn, is indicative of the amount of light impinging on the inner surface 1552 of the packaging material tube 1517. In response to this output, a determination can be made as to whether a sufficient fluence level is being achieved at the inner surface of the packaging material tube 1517 to effect decontamination of the packaging material tube 1517.

Advantageously, the present variation not only detects (indirectly) the amount of light generated by the flashlamp 1531, but, equally importantly, detects (directly) the amount of light impinging upon the inner surface of the packaging material tube 1517. Such is advantageous because these amounts (i.e., the amount of light generated and the amount of light impinging on the inner surface 1552) may differ in the event an outer surface 1578 of the outer safety glass 1528 is dirty.

In the event the fluence level at the inner surface 1552 of the packaging material tube 1517 is insufficient, i.e., below a prescribed threshold, e.g., 0.4 or 0.5 J/cm$^2$, power delivered to the flashlamp 1571 may be increased and/or operation of the packaging apparatus may be terminated until servicing can be performed.

Figure 16:
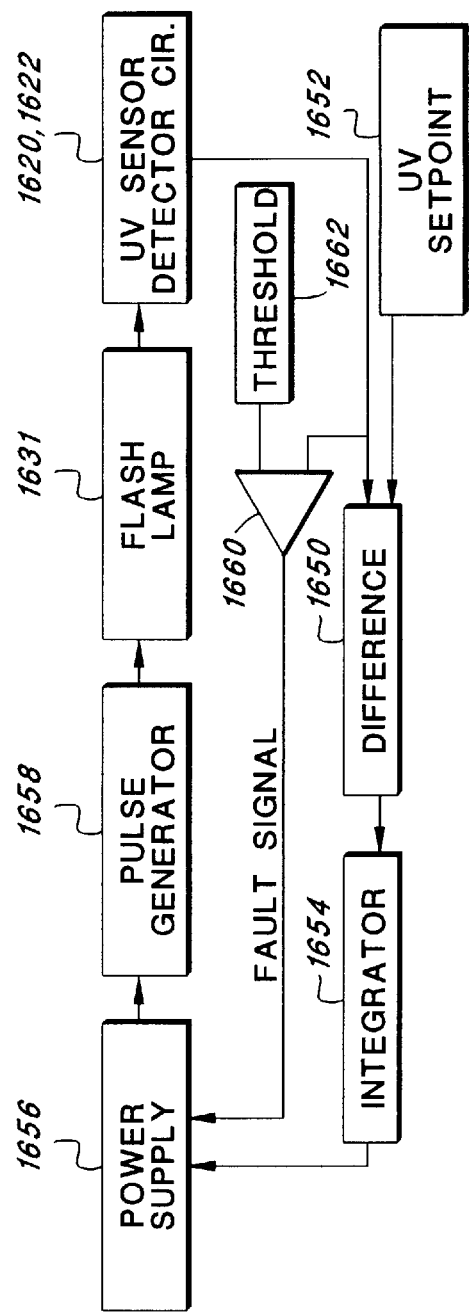
FIG. 16 is a block diagram showing a closed-loop feedback control system that may employ the fiber optic feedback system of FIG. 14.

Referring to FIG. 16, a block diagram is shown of a closed-loop feedback control system that may employ the fiberoptic feedback system of FIG. 15. Shown in block form is the UV-sensitive diode 1620 (or other suitable UV detector), the detector circuit 1622, and the flashlamp 1631. As shown, light from the flashlamp 1631 is conducted to a UV-sensitive diode/detector circuit 1620, 1622, which, as described above, determines an amount of light reaching the inner surface 1552 (FIG. 15) of the packaging material tube 1517 (FIG. 15) and/or an amount of light generated by the flashlamp 1631. As mentioned above, the UV-sensitive diode/detector circuit 1620, 1622 may include a sample-and-hold circuit that is reset prior to each flash of light. An output signal (i.e., a detection signal) from the UV detection system 1620, 1622 is directed to a difference circuit 1650. The detection signal is indicative of the amount of light reaching the inner surface 1552 (FIG. 15) of the packaging material tube 1517 (FIG. 15) and/or the amount of light generated by the flashlamp 1631, or when the UV-sensitive diode/detector circuit 1660, 1662 includes a sample-and-hold circuit, the peak amount(s) of such light. Also directed to the difference circuit 1650 is a set point signal from a UV set point circuit 1652.

The difference circuit 1650 determines a difference in the UV set point signal and the detection signal, and generates a difference signal in response thereto. The difference signal is directed to an integrator 1654, which provides a control signal to a power supply 1656. Alternatively, a proportional-integral-derivative (PID) device or other transfer function devices may be used in lieu of the integrator 1654. The control signal is used by the power supply 1656 to set a voltage level of a voltage output generated by the power supply 1656. The voltage signal is provided to a pulse generator 1658, and is used by the pulse generator 1653 to generate voltage pulses, which are provided to the flashlamp 1631, and cause the flashlamp to generate high-intensity, short-duration pulses of polychromatic light in the broad spectrum.

Advantageously, as the UV-sensitive diode/detector circuit 1620, 1622 detects progressively lower fluence levels impinging upon the inner surface of the packaging material tube 1517 (see FIG. 15), the difference signal generated by the difference circuit 1650 increases. As a result, the control signal generated by the integrator 1654 signals to the power supply 1656 to generate a larger voltage output, thus causing the amplitude of the voltage signal provided to the pulse generator 1658 to increase. This in turn causes the amplitude of the voltage pulses provided to the flashlamp 1631 by the pulse generator 1658 to increase, and therefore should cause the intensity of light produced by the flashlamp 1631 to increase. This increased flashlamp intensity, in turn, should normally result in an increase in fluence levels at the inner surface of the packaging material tube 1517 (FIG. 15), and a concomitant decrease in the difference signal.

Thus, a closed-loop feedback system is provided wherein as a detected fluence level at the inner surface 1552 of the packaging material tube 1517 decreases, the intensity of light generated by the flashlamp 1531 is increased so as to compensate for this decrease in detected fluence level. When an adequate fluence level is detected at the inner surface 1552 of the packaging material tube 1517, the intensity of the light generated by the flashlamp 1531 stops increasing. (In a similar manner, if the fluence level detected at the inner surface 1531 is too great, the intensity of the light generated by the flashlamp 1531 is decreased until an appropriate fluence level is detected.)

When the voltage level of the voltage pulses provided to the flashlamp 1631 can no longer be increased due to operational considerations, e.g., a prescribed amount less than a maximum voltage for the flashlamp 1631 and/or power supply 1656, and the fluence level detected by the UV-sensitive diode/detector circuit 1620, 1622 still falls below a desired fluence threshold indicated by a threshold circuit 1662, a fault signal generated by a comparator 1660 that compares the output signal from the UV-sensitive diode/detector circuit 1620, 1622 with a threshold signal from the threshold circuit 1662 can be used to trigger (or indicate) a fault condition. The fault signal can be used, for example, to trigger the halting of processing (i.e., sterilization, filling and sealing) of the packaging material tube 1517 (FIG. 15) until the aseptic packaging apparatus can be serviced, e.g., until either the flashlamp 1631 can be replaced and/or until the outer surface of the outer safety glass 1528 (see FIG. 15) can be cleaned of food product splash, ablated food product and/or presterilization agents.

Figure 17:
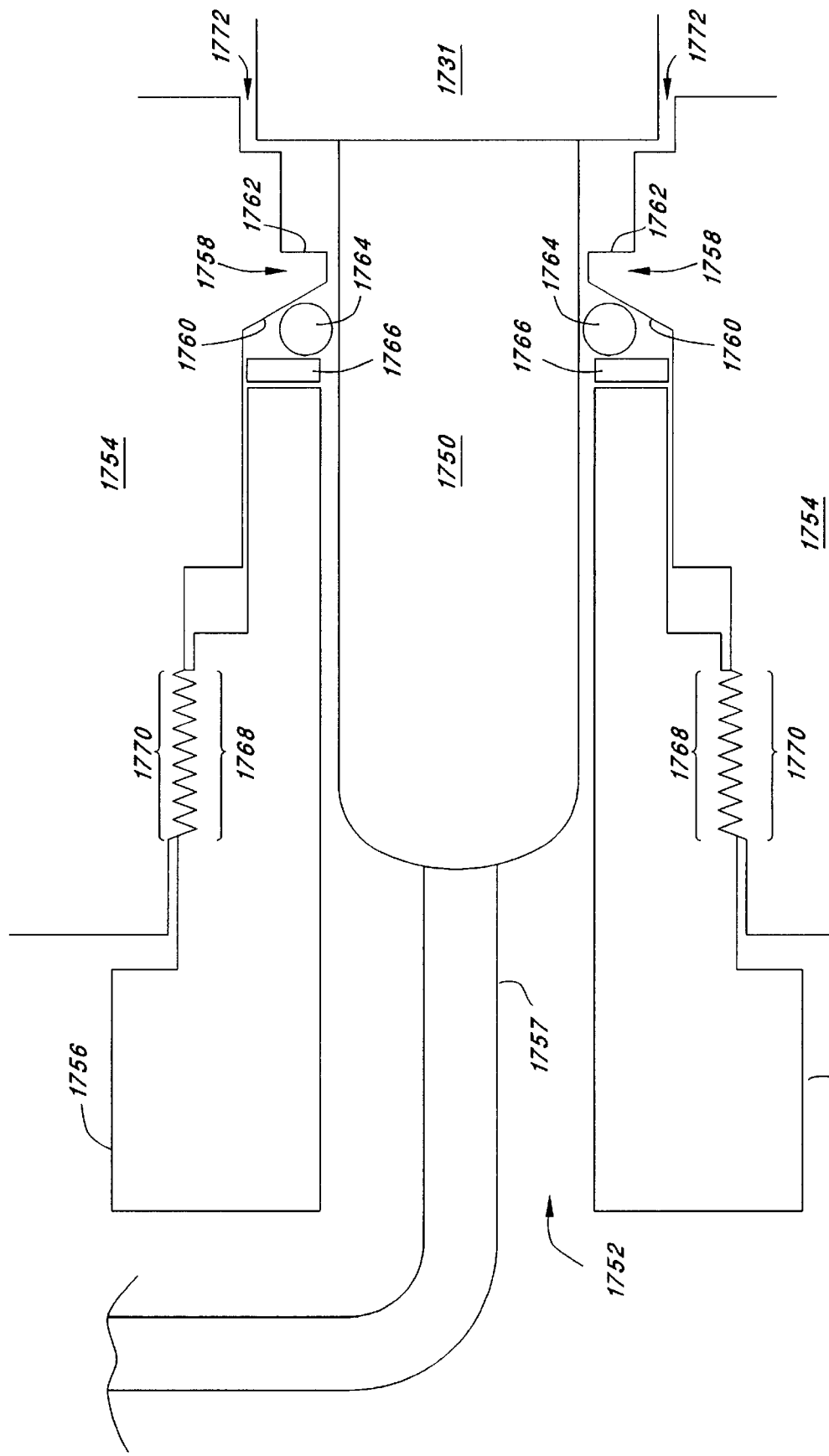
FIG. 17 is a cross-sectional view of a fastener system for securing a flashlamp into the one or the other variations of the light assemblies of FIGS. 8 and 11.

Referring to FIG. 17, a cross-sectional view is shown of a fastener system for securing respective ends of a flashlamp 1731 into the upper and/or lower holders of the variations of the light assemblies of FIGS. 8 and 11. Shown is the flashlamp 1731 having a metallic connector 1750, which passes into a holding cavity 1752 (or cylindrical cavity 1752). The holding cavity 1752 is formed by a portion of, for example, the lower holder 1754, which may be made from 25% glass-loaded Teflon, in combination with a compression cylinder 1756, which may be made from 25% glass-loaded Teflon. Connected to the metallic connector 1750 is a lead cable 1757 that provides an electrical current path to and/or from the flashlamp 1731. Integrated into, e.g., the lower holder 1754 within the cylindrical cavity 1752 is a frustioconical flange 1758. A frustioconical lower surface 1760 of the frustioconical flange 1758 is oriented to face generally away from the flashlamp 1731, and the frustioconical lower surface 1760 is at a less than ninety degree angle, e.g., a 45 degree angle, relative to an cylindrical exterior surface of the metallic connector 1750. A normal surface 1762 of the frustioconical flange 1758, which is preferably normal to an interior wall of the holding cavity 1752 and to the cylindrical exterior wall of the metallic connector 1750, is oriented to face toward the flashlamp 1731.

Interposed between the compression cylinder 1756 and the frustioconical lower surface 1760 of the frustioconical flange 1758 is a compressible rubber gasket 1764 (or O-ring 1764) that is juxtoposed against the frustioconical surface 1760, and a slip washer 1766 that is juxtaposed against the compression cylinder 1756. The compression cylinder 1756 includes a threaded portion 1768 that mates with a threaded portion 1770 of the lower holder 1754.

When the compression cylinder 1756 is rotated, e.g., in a clockwise direction, in response to a rotational vector force oriented, e.g., toward the flashlamp 1731, the threaded portion 1768 of the compression cylinder 1756, in combination with the threaded portion 1778 of the lower holder 1754, causes a compressive force to be directed against the slip washer 1766 in a direction parallel to a center axis of the cylindrical cavity 1752 and oriented toward the frustioconical flange 1758. In response to such force, the slip washer 1766 is compressed against the gasket 1764, which is in turn compressed against the frustioconical surface 1760 of the frustioconical flange 1758.

In response to the force against the gasket 1764, the gasket 1764 is directed radially inward against the metal connector 1750 by the frustioconical surface 1760. This causes a seal to form between the metal connector 1750, the gasket 1764, and the frustioconical flange 1758.

Advantageously, this prevents cooling water from flowing from a region 1772 outside the flashlamp 1731 and within the water jacket into the cylindrical cavity 1752 and out of the lower holder 1754. Advantageously, such seal is formed regardless of inconsistencies in the length of the flashlamp 1731, and in a manner tolerant of inconsistencies in the diameter of the flashlamp 1731.

Furthermore, the variation shown can be adapted such that a glass portion of the flashlamp 1731 projects downward into the cylindrical cavity 1752 such that the seal is formed between the glass portion of the flashlamp 1731 and the frustioconical flange 1758 (as opposed to between the metal connector 1750 and the frustioconical surface 1760, as depicted). In this way, the cooling water can be prevented from coming into contact with the metal connector 1750, which may be advantageous in particular applications of the present variation.

Figure 18:
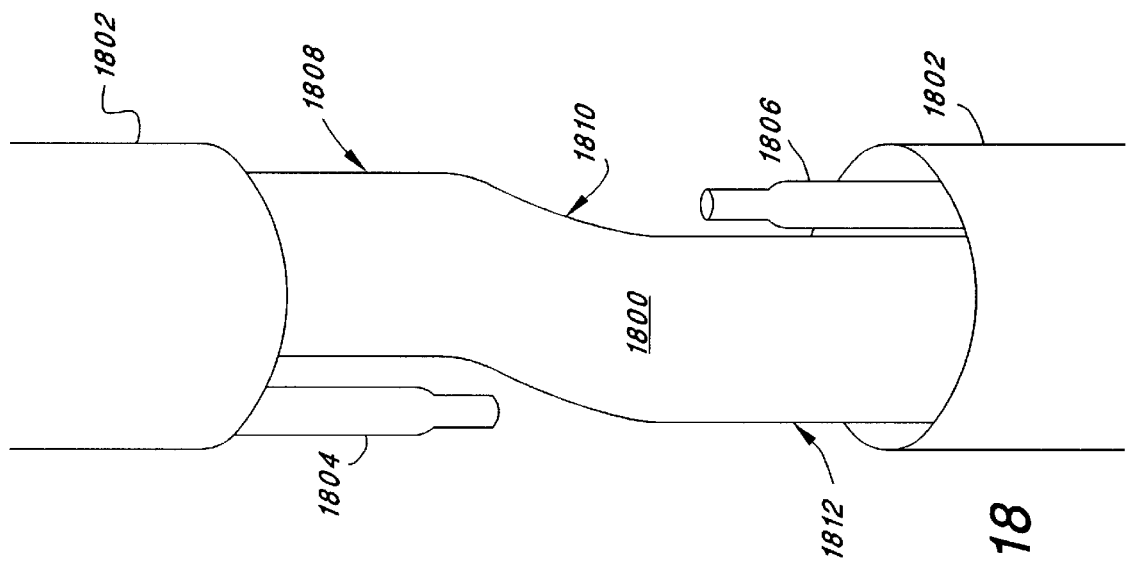
FIG. 18 is a perspective view of an alternative lamp assembly geometry employable in the lamp assemblies of FIGS. 8 and 11 to minimize the diameter of the lamp assemblies, thereby reducing the minimum diameter of a packaging material tube with which such lamp assemblies may be employed.

Referring to FIG. 18, a perspective view is shown of an alternative flashlamp assembly geometry employable in the flashlamp assemblies of FIGS. 8 and 11 to minimize diameter of the flashlamp assemblies, thereby reducing a minimum diameter of a packaging material tube with which the flashlamp assemblies may be employed. Shown is the fill pipe 1800, a reduced diameter packaging material tube 1802 (partially cut away), and first and second flashlamps 1804, 1806. The reduced diameter packaging material tube 1802 may, for example, have a diameter of from about 3 cm and 7 cm, e.g., 5 cm. An outer safety glass (not shown) may be employed, as with embodiments of FIGS. 8 and 11, but has been omitted from FIG. 18 to increase the clarity of FIG. 18.

The first flashlamp 1804 is juxtaposed within the reduced diameter packaging material tube 1802 along an upper portion 1808 of the fill pipe 1800. Within the reduced diameter packaging material tube 1802, the upper portion 1808 of the fill pipe 1800, and the upper flashlamp 1804 lie in parallel juxtaposition, with the upper portion 1808 positioned to the right, as oriented in FIG. 18, and with the upper flashlamp 1804 positioned to the left.

Below the upper portion 1808 of the fill pipe 1800, and the first flashlamp 1804 (or upper flashlamp 1804) is a transitional portion 1810 of the fill pipe 1800. The transitional portion 1810 represents an offset region of the fill pipe 1800 that transitions from the upper portion 1808 to a lower portion 1812 of the fill pipe 1800.

The lower portion 1812 is in parallel juxtaposition with the second flashlamp 1806 (or lower flashlamp 1806). Within the reduced diameter packaging material tube 1802, the lower portion 1812 is positioned to the left, as oriented in FIG. 18, and the lower flashlamp 1806 is positioned to the right, thus occupying opposite sides of reduced diameter packaging material tube 1820 from the sides occupied by the upper portion 1808 and the upper flashlamp 1804.

Thus, the transitional portion 1810 transitions the fill pipe 1800 from the right side of the reduced diameter packaging material tube 1802 to the left side of the reduced diameter packaging material tube 1802, as oriented in FIG. 18. This transition allows space within the packaging material tube for the upper flashlamp 1804 to be positioned to the left of the fill pipe 1800, and space within the packaging material tube 1800 for the lower flashlamp 1806 to be positioned to the right of the fill pipe 1800, while still accommodating the reduced diameter packaging material tube 1802.

In this way, the upper flashlamp 1804 and the lower flashlamp 1806, when operated in concert as the reduced diameter packaging material tube 1802 passes over the upper and lower flashlamps 1804, 1806, are able to expose the entire interior surface (both the right side and the left side) of the reduced diameter packaging material tube 1802 to one or more pulses of high-intensity, short-duration, broad-spectrum polychromatic light.

At the same time, however, the amount of interior space, i.e., diameter, needed to envelope both the fill pipe 1800 and the upper and lower flashlamps 1804, 1806 within the reduced diameter packaging material tube 1802, as compared to heretofore known approaches, is significantly reduced.

Referring to FIG. 19, a cross-sectional view is shown of a further variation of a light assembly, which may be part of the other embodiment of the aseptic packaging assembly as shown in FIGS. 3 and 4. Shown are an outer safety glass 1900, a U-shaped flashlamp 1902 (or U-lamp 1902) having a first metal electrode 1904, a second metal electrode 1906, a first O-ring 1908, a second O-ring 1910 and a third O-ring 1912. Also shown, is a flashlamp receptacle 1914 including a flashlamp holding device 1915 that provides for non-uniformities in U-lamp electrode spacing.

In operation, the electrodes 1904, 1906 of the U-lamp 1902 are inserted into the flashlamp receptacle 1914 (or flashlamp holder 1914) such that the first O-ring 1908 seals the first electrode 1904 against inner walls of a first socket 1916 of the flashlamp holder 1914. Within a second socket 1918 of the flashlamp holder 1914, the lamp-holding device 1915 receives the second electrode 1906, with the second O-ring 1910 sealing the second electrode 1906 against an interior surface of the flashlamp holding device 1915, and with the third O-ring 1912 sealing an exterior surface of the flashlamp holding device 1915 against an interior surface of the second receptacle 1918.

Advantageously, the second O-ring 1910 is positioned against the interior surface of the flashlamp holding device 1915 within a first channel 1920 formed adjacent to a rib 1922 that protrudes into the interior of the flashlamp holding device 1915. This rib 1922 prevents the second O-ring from rolling within the flashlamp holding device 1915 beyond a prescribed range within the flashlamp holding device. The first channel is located proximal to the U-lamp 1912 along an inner circumference of the flashlamp holding device 1915, which is generally cylindrical.

The third O-ring 1912 is positioned within another channel 1924 formed between a pair of ribs 1926 that protrude radially outward from the flashlamp holding device 1915. The other channel 1924 is located distally relative to the U-lamp 1902 at the opposite end of the flashlamp holding device 1915 from the channel 1920 in which the second O-ring 1910 is positioned. As with the second O-ring 1910, the other channel prevents the third O-ring 1906 from rolling over the exterior of the flashlamp holding device 1915 beyond a prescribed range defined by the pair of ribs 1926.

Advantageously, the flashlamp holding device 1915 is made from a rigid metal material, such as stainless steel, and the proximal end of the flashlamp holding device 1915 allowed to be displaced laterally relative to the distal end of the flashlamp holding device. In this way, the flashlamp holding device 1915 advantageously overcomes the problem of inconsistencies in distance between the U-lamp's first and second electrodes 1904, 1906, while, advantageously, at the same time maintaining a water tight seal between the receptacle 1914 and the electrodes 1904, 1906.

Such water tight seal advantageously allows water to be circulated in a sealed fluid circuit, which includes a space within the outer safety glass 1900, but outside the U-lamp 1902. This water, such as is known in the art, provides cooling for the U-lamp 1902, thereby enhancing the useful life if the U-lamp 1902 and increasing the flash repetition rate at which the U-lamp 1902 can be utilized, and furthermore may provide spectral filtration of light emanating from the U-lamp 1902

Referring to FIG. 20, a detailed cross-sectional view is shown of the flashlamp holding device 2000. Shown are the second electrode 2002, the second O-ring 2004, the third O-ring 2006, the flashlamp holding device 2000 and the second socket 2008 of the receptacle 2010. As can be seen, the electrode 2002 has been inserted into the flashlamp holding device 2000 within the second socket 2008, with the second O-ring 2004 being positioned within the channel 2012 formed at the interior circumference of the flashlamp holding device 2000 at its proximal end. The third O-ring 2008 is positioned between the interior surface of the second socket 2008, and the other channel 2014 at the exterior of the distal end of the flashlamp holding device 2000.

Referring to FIG. 21, another detailed cross-sectional view is shown of the flashlamp holding device 2100, wherein a non-uniform U-lamp has been employed. Shown are the second electrode 2102, the second socket 2104 of the receptacle 2106, the flashlamp holding device 2100, the second O-ring 2108 and the third O-ring 2110.

As can be seen, the proximal end of the flashlamp holding device 2100 is displaced transversely relative to the distal end of the flashlamp holding device 2100 in order to accommodate a non-uniform distance between the U-lamp's electrodes. Such displacement of the proximal end, i.e., the end proximate to the U-lamp, of the flashlamp holding device 2100 forces the proximal end of the flashlamp holding device closer to one interior surface of the second socket 2104 than another interior surface of the second socket 2104.

Advantageously, seal integrity is maintained by the second and third O-rings 2108, 2110, while at the same time accommodating the non-uniform U-lamp. Thus, the flashlamp holding device advantageously reduces the precision with which the U-lamps used therewith must be manufactured, thereby decreasing waste and significantly reducing costs.

Figure 22:
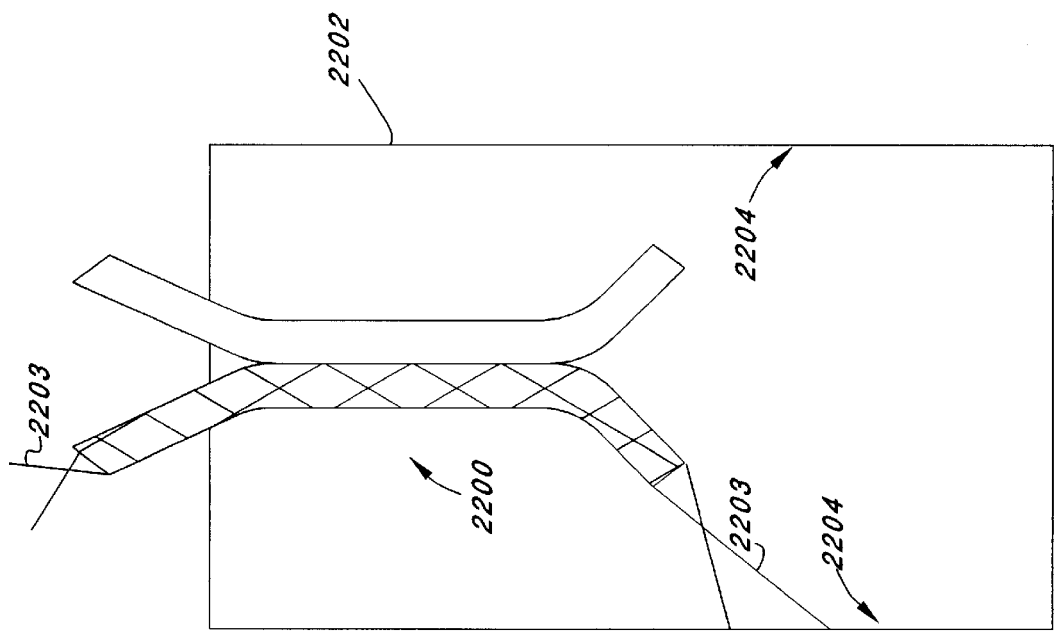
FIG. 22 is a schematic view of one embodiment of a light guide that may be employed along with a linear flashlamp instead of a U-lamp in the aseptic packaging assembly as shown in FIGS. 3 and 4.

Referring to FIG. 22, a schematic view is shown of one embodiment of a light guide 2200 that may be employed along with a linear flashlamp (not shown) in the aseptic packaging assembly shown in FIGS. 3 and 4, so as to eliminate need for the U-shaped flashlamps (U-lamps) and the problems attendant therewith, such as cost and imprecision in electrode spacing. The light guide is shown lowered into a packaging material cup 2202 so as to project high-intensity, short-duration pulses of broad-spectrum polychromatic light 2203 from the linear flashlamp onto interior surfaces 2204 of the packaging material cup 2202. Preferably, the light guide 2200 is made from a material such as quartz that is an excellent light conductor over a broad spectrum.

Figure 23:
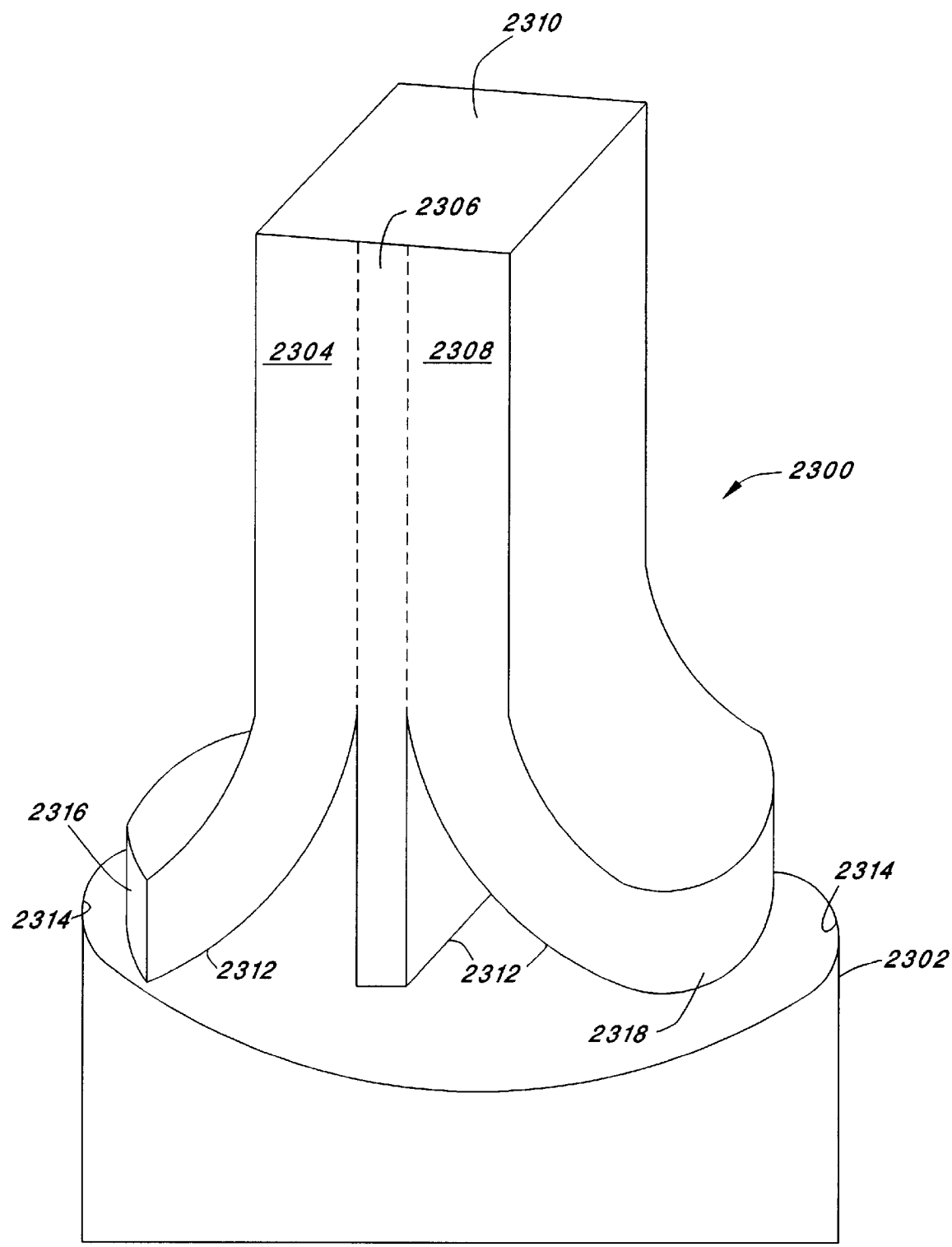
FIG. 23 is a perspective view of one variation of the embodiment of the light guide of FIG. 22.

Referring to FIG. 23, a perspective view is shown of one variation of the embodiment of the light guide of FIG. 22. As can be seen, the light guide 2300 is positioned above a packaging material cup 2302. The light guide employs three quartz layers 2304, 2306, 2308, which at an upper end 2310 are approximately rectangular in cross-section and oriented to direct light generally downward as oriented in FIG. 23. At a lower end 2312 of the layers 2304, 2306, 2308, a middle layer 2306 continues its downward orientation, so as to project light onto a bottom surface of the packaging material cup 2302. Each of two side layers 2304, 2308 curve away from the middle layer 2306 toward an interior side surface 2314 of the packaging material cup 2302. Edges 2316, 2318 of the side layers 2304, 2308 curve such that when the light guide viewed from above, as oriented in FIG. 23, the light guide appears to be generally circular in cross-section, thereby facilitating insertion of the light guide 2300 into the packaging material cup 2302, which is circular in interior cross-section.

In operation, high-intensity, short-duration pulses of polychromatic light in a broad spectrum are projected onto an upper surface of the light guide 2300 at its upper end 2310. The pulses of light enter the light guide 2300 through such upper surface. Light entering the middle layer 2306 is projected through the light guide in a downward direction. Such light emerges from the light guide 2300 and is projected onto the bottom of the packaging material cup 2302. Light entering each of the side layers 2304, 2308 is directed by the light guide 2300 in generally a downward direction, but near the lower end 2312 of the light guide the light is directed away from the middle layer 2306 by the side layers 2304, and toward the interior side surface 2314 of the packaging material cup 2302. Such light then emerges from the side layers 2304, 2308 and is projected onto the interior side surface 2314 of the packaging material cup 2302.

By moving the light guide up and down within the packaging material cup 2302 during successive flashes of the linear flashlamp, and by rotating either the packaging material cup 2302 or the light guide 2300 during such successive flashes, the entire interior surface 2314 of the packaging material cup 2302 may be treated with high-intensity, short-duration pulses of broad-spectrum polychromatic light without the need for U-shaped flashlamps.

Advantageously, the present variation therefore overcomes the problems associated with U-lamps, as well as avoids the higher costs of U-lamps as compared to linear flashlamps, by providing an alternative to the usage of U-lamps for treating packaging material cups.

Figure 24:
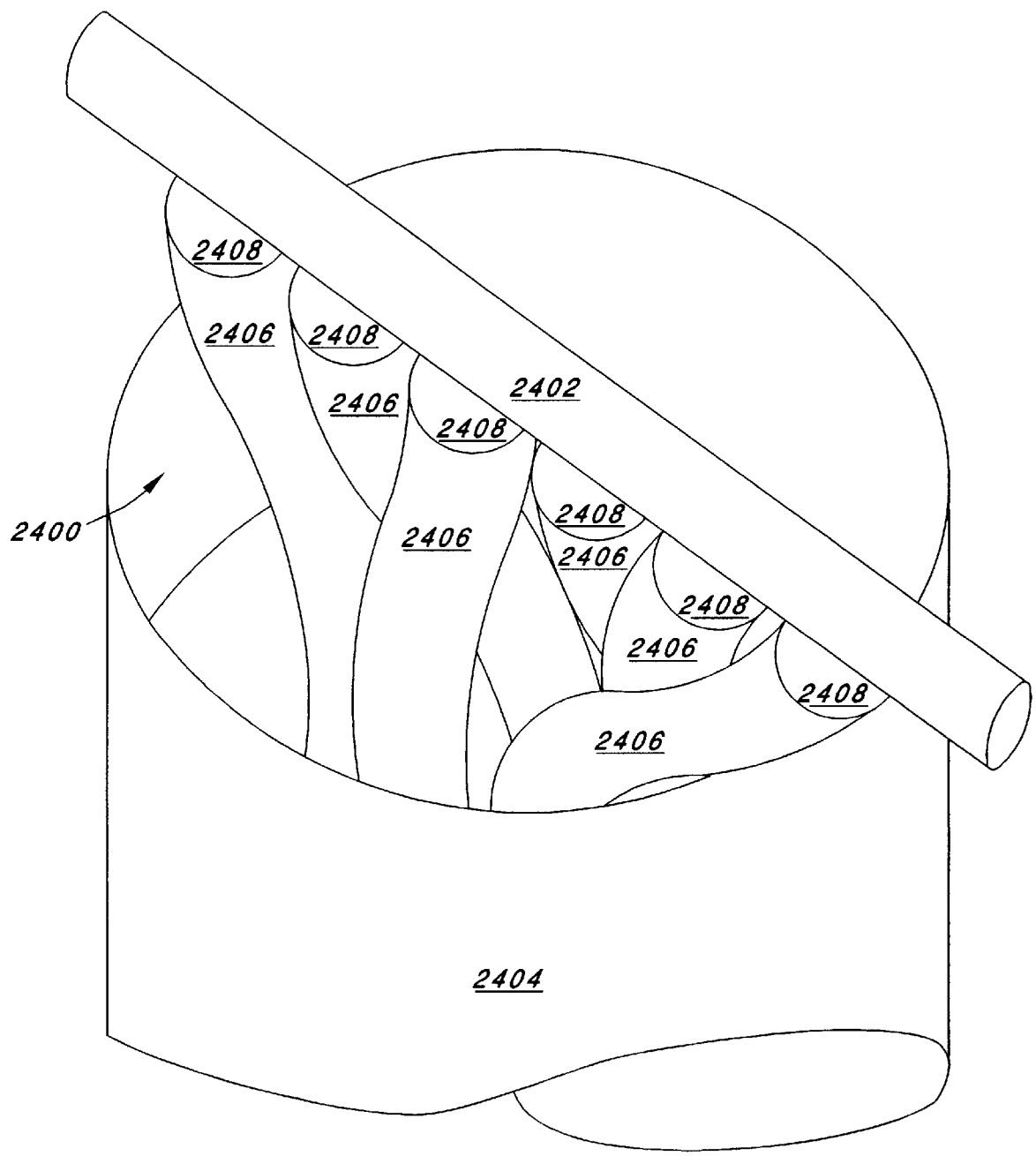
FIG. 24 is a perspective view from above of one variation on another embodiment of a light guide that may be employed along with a linear flashlamp in the aseptic packaging assembly in FIGS. 3 and 4.

Referring to FIG. 24, a perspective view is shown from above of another variation of the embodiment of a light guide 2400 that may be employed along with a linear flashlamp 2402 in the aseptic packaging assembly in FIGS. 3 and 4. Shown are the linear flashlamp 2402, a packaging material cup 2404 and a plurality of bent quartz rods 2406 each oriented with an upper end 2408 positioned along a portion of the linear flashlamp 2402. Preferably, a reflector (not shown) focuses light emitted from upper portions (as oriented in FIG. 24) of the flashlamp 2402 downwardly into the upper ends 2408 of the bent quartz rods 2406.

In operation, light emitted from the linear flashlamp 2402 is received into the upper ends 2408 of the bent quartz rods 2406 and carried generally downwardly by the bend quartz rods.

Figure 25:
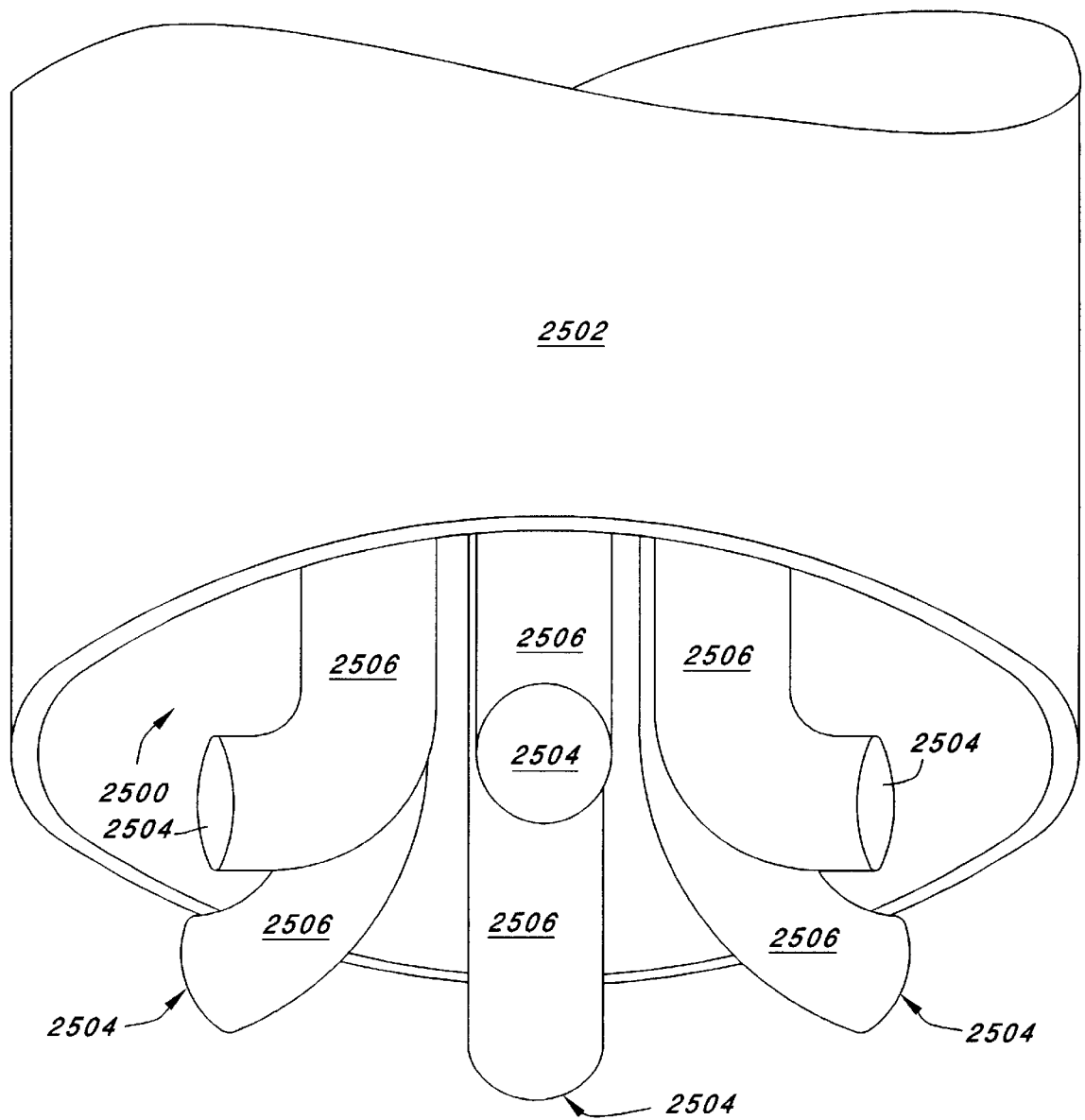
FIG. 25 is a perspective partially cutaway view from below of the variation of the other embodiment of the light guide of FIG. 24.

Referring to FIG. 25, a perspective view, partially cutaway, is shown from below the variation of the embodiment of the light guide 2500 also shown in FIG. 24. Shown is a cutaway view of the packaging material cup 2502 along with lower ends 2504 of the bent quartz rods 2506. As can be seen, the lower ends 2504 of the bent quartz rods 2506 are oriented so as to direct light 2504 generally downwardly. Each lower end 2504 is bent outwardly toward the interior side surface of the packaging material cup 2502 and is oriented such that there is an approximately 60 degree displacement between each of the outwardly bent lower ends 2504.

In operation, light carried by the bent quartz rods 2506 from the linear flashlamp is directed downwardly into the packaging material cup 2502 until it reaches the lower ends 2504 of the bent quartz rods 2506. At the lower ends 2504 of the bent quartz rods 2506, the light is directed outwardly toward the interior side surface of the packaging material cup 2502. Advantageously, by orienting each lower end 2504 at a 60 degree angular displacement relative to neighboring lower ends 2504, maximal dispersion of the light carried in the bent quartz rods 2506 throughout the entire interior circumference of the packaging material cup 2502 is achieved.

In practice, the light guide 2506 is moved up and down within the packaging material cup 2502 during successive high-intensity, short-duration pulses of broad-spectrum polychromatic light, so as to expose the entire interior side and bottom surfaces of the packaging material cup 2502 to such light.

In this way, an embodiment is provided through which the interior surface of the packaging material cup 2502 can be exposed to high-intensity, short-duration pulses of broad-spectrum polychromatic light without the need for a U-lamp, which has heretofore been the convention.

While the invention herein disclosed has been described by means of specific embodiments and applications thereof, numerous modifications and variations could be made thereto by those skilled in the art without departing from the scope of the invention set forth in the claims.

What is claimed is:

1. An apparatus for deactivating microorganisms comprising:
    a flashlamp;
    packaging material moving means for moving packaging material relative to the flashlamp in order to sequentially expose portions of the packaging material to high-intensity, short-duration pulses of polychromatic light in a broad spectrum emitted from the flashlamp;
    a water jacket surrounding the flashlamp; and
    an external coating applied to first and second ends of the water jacket.

2. The apparatus of claim 1 wherein the external coating includes a Teflon-containing coating.

3. The apparatus of claim 1 further comprising:
    an outer safety glass surrounding the water jacket and the flashlamp; and
    another external coating applied to first and second ends of the outer safety glass.

4. The apparatus of claim 1 wherein the external coating includes a Platinum-containing coating.

5. The apparatus of claim 4 further comprising:
    another external coating at least partially covering the Platinum-containing coating.

6. The apparatus of claim 5 wherein the other external coating includes a Teflon-containing coating.

7. An apparatus for deactivating microorganisms comprising:
    a first flashlamp;
    a second flashlamp;
    a fill pipe including, a first portion juxtaposed with the first flashlamp, and a second portion juxtaposed with the second flashlamp, the first portion being positioned to occupy a first side of a packaging material tube, and the first flashlamp being positioned to occupy a second side of the packaging material tube, as the packaging material tube is passed over the first portion and the first flashlamp juxtaposed therewith, and the second portion being positioned to occupy the second side of the packaging material tube, and the second portion being positioned to occupy the first side, and the second flashlamp being positioned to occupy the second side, as the packaging material tube is passed over the second portion and the second flashlamp juxtaposed therewith.

8. The apparatus of claim 7 wherein said first flashlamp is a Xenon flashlamp.

9. The apparatus of claim 7 wherein said packaging material tube is a laminate including at least one polyethylene layer.

10. An apparatus for deactivating microorganisms comprising:
    a first linear flashlamp;
    a first water jacket enveloping the first linear flashlamp;
    a first cooling water conduit formed between an exterior of the first linear flashlamp and an interior of the first water jacket;
    a second linear flashlamp;
    a second water jacket enveloping the second linear flashlamp;
    a second cooling water conduit formed between an exterior of the second linear flashlamp and an interior of the first water jacket;
    a fill pipe juxtaposed between the first water jacket and the second water jacket;
    a sterile air pipe enveloping the fill pipe;
    a sterile air conduit formed between an exterior of the fill pipe and an interior of the sterile air pipe;
    a reflector enveloping the sterile air pipe; and
    an outer safety glass enveloping the first water jacket, the second water jacket, and the reflector.

11. The apparatus of claim 10 further comprising:
    a water return conduit formed between an exterior of the first water jacket, the second water jacket, and the reflector, and an interior of the outer safety glass.

12. The apparatus of claim 10 further comprising:
    a reflective material enveloping the outer safety glass.

13. The apparatus of claim 12 wherein said reflective material comprises a packaging material.

14. An apparatus for deactivating microorganisms comprising:
    a first linear flashlamp;
    a second linear flashlamp;
    a fill pipe interposed between the first linear flashlamp and the second linear flashlamp;
    a sterile air pipe enveloping the fill pipe;
    a sterile air conduit formed between an exterior of the fill pipe and an interior of the sterile air pipe; and
    an outer safety glass enveloping the first flashlamp, the second flashlamp and the sterile air pipe.

15. The apparatus of claim 14 further including:
    a reflectorized coating applied to an exterior of the sterile air pipe; and
    a cooling water conduit formed between an exterior of the second linear flashlamp, the first linear flashlamp and the sterile air pipe, and an interior of the outer safety glass.

16. The apparatus of claim 15 further comprising:
    a reflective material enveloping the outer safety glass.

17. The apparatus of claim 16 wherein said reflective material comprises a packaging material.

18. The apparatus of claim 15 further including:
    a first exterior coating applied to a first end of the first water jacket, and a second exterior coating applied to a second end of the first water jacket.

19. The apparatus of claim 18 wherein said first exterior coating and said second exterior coating comprise Platinum-containing coatings.

20. The apparatus of claim 18 wherein said first exterior coating and said second exterior coating comprise Teflon-containing coatings.

21. The apparatus of claim 18 further including:
    a third exterior coating applied over said first exterior coating to said first end of said first water jacket, and a fourth exterior coating applied over said second exterior coating to said second end of said first water jacket.

22. The apparatus of claim 21 wherein said first exterior coating and said second exterior coating comprise Platinum-containing coatings, and wherein said third exterior coating and said fourth exterior coating comprise Teflon-containing coatings.

23. An apparatus for deactivating microorganisms comprising:

a flashlamp; and a first holder including a first lamp holding device including:

a holding cylinder including a first flange having a first frustioconical surface, a first end of the flashlamp being positioned in the holding cylinder and extending past the first flange, the first frustioconical flange being at a less than ninety degree angle relative to an exterior of the flashlamp;

a first O-ring juxtaposed against the frustioconicell surface; and a first compression cylinder for applying a first force to the first O-ring that compresses the first O-ring against the first frustioconical surface, wherein the frustioconical surface, in combination with the first force, causes the first O-ring to compress against the flashlamp so as to form water tight seals between the first O-ring and the first frustioconical surface, and the first O-ring and the flashlamp.

24. The apparatus of claim 23 further including:

a first set of threads on an exterior of the first compression cylinder; and a second set of threads on an interior of the holding cylinder positioned so as to engage the first set of threads upon insertion of the compression cylinder into the holding cylinder.

25. The apparatus of claim 23 further comprising:

a second holder including a second lamp holding device including:

a holding cylinder including a second flange having a second frustioconical surface, a second end of the flashlamp being positioned in the holding cylinder and extending past the second flange, the second frustioconical flange being at a less than ninety degree angle relative to an exterior cf the flashlamp;

a second O-ring juxtaposed against the frustioconical surface; and a second compression cylinder for applying a second force to the second O-ring that compresses the second O-ring against the second frustioconical surface, wherein the frustioconical surface, in combination with the second force, causes the second O-ring to compress against the flashlamp so as to form water tight seals between the second O-ring and the second frustioconical surface, and the second O-ring and the flashlamp.

26. The apparatus of claim 25 further comprising:

a fill pipe juxtaposed with the flashlamp;

a sterile air pipe enveloping the fill pipe; and an outer safety glass enveloping the flashlamp, and the sterile air pipe.

27. The apparatus of claim 26 further comprising:

a sterile air conduit formed between an exterior of the fill pipe and an interior of the sterile air pipe.

* * * * *